United States Patent
Fotsch et al.

(10) Patent No.: US 8,090,590 B2
(45) Date of Patent: Jan. 3, 2012

(54) ELECTRONIC PERSONAL HEALTH RECORD SYSTEM

(75) Inventors: Edward J. Fotsch, Sausalito, CA (US); Leslie Yuan, San Francisco, CA (US)

(73) Assignee: Intuit Inc., Mountain View, CA (US)

( * ) Notice: Subject to any disclaimer, the term of this patent is extended or adjusted under 35 U.S.C. 154(b) by 1242 days.

(21) Appl. No.: 11/208,144

(22) Filed: Aug. 19, 2005

(65) Prior Publication Data

US 2006/0229918 A1     Oct. 12, 2006

Related U.S. Application Data

(63) Continuation-in-part of application No. 11/085,984, filed on Mar. 21, 2005, which is a continuation-in-part of application No. 10/387,041, filed on Mar. 10, 2003, and a continuation-in-part of application No. 10/641,982, filed on Aug. 15, 2003.

(51) Int. Cl.
    G06Q 10/00    (2006.01)
    G06Q 50/00    (2006.01)
(52) U.S. Cl. .................................. 705/2; 705/3; 705/4
(58) Field of Classification Search .................. 705/2–4; 358/1.14, 1.15; 707/999.009
    See application file for complete search history.

(56) References Cited

U.S. PATENT DOCUMENTS

| | | | |
|---|---|---|---|
| 4,319,336 A | 3/1982 | Anderson et al. | |
| 4,650,981 A | 3/1987 | Foletta | |
| 5,478,211 A | 12/1995 | Dominiak et al. | |
| 5,589,892 A | 12/1996 | Knee et al. | |
| 5,597,072 A | 1/1997 | Lieberman et al. | |
| 5,862,223 A | 1/1999 | Walker et al. | |
| 5,899,998 A | 5/1999 | McGauley et al. | |
| 5,930,759 A | 7/1999 | Moore et al. | |
| 5,954,641 A | 9/1999 | Kehr et al. | |
| 5,974,389 A | 10/1999 | Clark et al. | |
| 6,039,688 A | 3/2000 | Douglas et al. | |
| 6,151,586 A | 11/2000 | Brown | |
| 6,171,112 B1 | 1/2001 | Clark et al. | |
| 6,208,973 B1 | 3/2001 | Boyer et al. | |
| 6,272,472 B1 | 8/2001 | Danneels et al. | |
| 6,381,029 B1 * | 4/2002 | Tipirneni | 358/1.14 |
| 6,516,315 B1 | 2/2003 | Gupta | |
| 6,654,724 B1 | 11/2003 | Rubin et al. | |

(Continued)

OTHER PUBLICATIONS

International Search Report & The Written Opinion of the International Searching Authority, Patent Cooperation Treaty, Application No. PCT/US06/09968, Sep. 25, 2007.

(Continued)

*Primary Examiner* — Gerald J. O'Connor
*Assistant Examiner* — Michelle Le
(74) *Attorney, Agent, or Firm* — Gunnison, McKay & Hodgson, L.L.P.; Philip McKay

(57) ABSTRACT

Methods and apparatus for providing access to information associated with a patient are disclosed. Information associated with a patient may be stored electronically, enabling the information from an electronic health record (e.g., electronic personal health record controlled by a patient) or a portion thereof to be provided to an entity such as a healthcare provider. Patient records may be maintained and controlled by multiple entities, such as the healthcare providers, patients, payors, or other third parties. Information from these records may be transferred among these entities, thereby enabling updates to such records to be performed. These updates may occur automatically or upon acceptance by the receiving entity (e.g., patient or healthcare provider).

8 Claims, 17 Drawing Sheets

U.S. PATENT DOCUMENTS

| | | | |
|---|---|---|---|
| 6,988,075 B1* | 1/2006 | Hacker | 705/3 |
| 7,174,368 B2 | 2/2007 | Ross, Jr. | |
| 2001/0056359 A1 | 12/2001 | Abreu | |
| 2002/0029157 A1* | 3/2002 | Marchosky | 705/3 |
| 2002/0072934 A1 | 6/2002 | Ross et al. | |
| 2002/0123909 A1 | 9/2002 | Salisbury et al. | |
| 2002/0128865 A1 | 9/2002 | Alten | |
| 2002/0128870 A1 | 9/2002 | Whitson | |
| 2002/0138306 A1 | 9/2002 | Sabovich | |
| 2002/0156650 A1 | 10/2002 | Klein et al. | |
| 2003/0018495 A1 | 1/2003 | Sussman | |
| 2003/0023269 A1 | 1/2003 | den Boer | |
| 2003/0023562 A1 | 1/2003 | Bailey et al. | |
| 2003/0028399 A1 | 2/2003 | Davis et al. | |
| 2003/0040940 A1 | 2/2003 | Nehammer | |
| 2003/0088440 A1* | 5/2003 | Dunn | 705/3 |
| 2003/0088452 A1 | 5/2003 | Kelly | |
| 2003/0188200 A1 | 10/2003 | Paquin et al. | |
| 2003/0214630 A1 | 11/2003 | Winterbotham | |
| 2004/0073453 A1 | 4/2004 | Nenov et al. | |
| 2004/0172307 A1* | 9/2004 | Gruber | 705/3 |
| 2004/0186884 A1 | 9/2004 | Dutordoir | |
| 2004/0220829 A1 | 11/2004 | Baharav et al. | |

OTHER PUBLICATIONS

International Search Report & The Written Opinion of the International Searching Authority, Patent Cooperation Treaty, Application No. PCT/US06/31774, Sep. 24, 2007.

Non-Final Office Action, United States Patent & Trademark Office, U.S. Appl. No. 10/387,041, filed Mar. 10, 2003, Aug. 9, 2007.

Response to Non-Final Office Action, U.S. Appl. No. 10/387,041, filed Mar. 10, 2003, Dec. 10, 2007.

Non-Final Office Action, United States Patent & Trademark Office, U.S. Appl. No. 10/641,982, filed Aug. 15, 2003, Jul. 26, 2007.

Response to Non-Final Office Action, U.S. Appl. No. 10/641,982, filed Aug. 15, 2003, Nov. 21, 2007.

Acuff, Richard D., Fagan, M.D., Ph.D, Lawrence M., Rindfleisch, M.S., Thomas C., Levitt, Benajmin J., Ford, M.D., Paul M., "Lightweight, Mobile E-Mail for Intra-Clinic Communication," Jun. 1997, Stanford University School of Medicine, Section on Medical Informatics, p. 4.

Final Office Action, United States Patent & Trademark Office, U.S. Appl. No. 10/387,041, filed Mar. 10, 2003, Mar. 5, 2008.

Final Office Action, United States Patent & Trademark Office, U.S. Appl. No. 10/641,982, filed Aug. 15, 2003, Mar. 7, 2008.

Schatz, Elizabeth, "Reaching a Doctor by E-Mail," Tuesday, Apr. 15, 2003, Wall Street Journal, p. 4.

Parker-Pope, Tara, "Virtual Second Opinions: When the Web Can Be Better Than Seeing a Local Doc," Health Journal.

Website, "The Healthy Email Project," [http://www.msu.edu/~healthy/page/project.html], Copyright 2001 Healthy Email Project, Michigan State University.

Website, "Powerful Technology Enabling Stronger Healthcare Partnerships," [https://www.mydoconlin.com/Marketing/index.html], MyDocOnline (TM), tools for modern health care, Copyright 2003 MyDocOnline, Inc. All Rights Reserved.

Website, "Health Plan Benefits," Relay Health (SM) Secure Online Communication for Healthcare, [https://www.relayhealth.com/rh/specific/healthPlans/default.aspx], Copyright 1999-2003 RelayHealth Corporation. All Rights Reserved.

Non-Final Office Action, United States Patent & Trademark Office, U.S. Appl. No. 11/086,118, filed Mar. 21, 2005, Feb. 18, 2009.

US Food and Drug Admin., "Sign up for FDA's Free E-Mail Lists," navigated from www.recalls.gov obtained via http://web.archive.org for the date Mar. 19, 2004, http://web.archive.org/web/20040214031829/www.fda.gov/emaillist.html.

Vitros Immunodiagnostic Products, "Urgent Product Correction/Recall Notification," Oct. 25, 2004.

US Food and Drug Admin, "Patient and Physician Attitudes and Behaviors Associated With DTC Promotion of Prescription Drugs—Summary of FDA Survey Research Results," Nov. 19, 2004, Appendix B.3 2002 Physician Survey.

Response to Non-Final Office Action dated May 28, 2009, U.S. Appl. No. 11/086,118, filed Mar. 21, 2005.

* cited by examiner

Patients First See Their Existing Demographic Data, Verify/Edit & Continue

Medem — Connecting Physicians and Patients

Home | Message Inbox | Education Programs | Health Record | My Clinicians

Permissions | Messages

Print | Help

Registration Information

<< instructional text goes here >>

[Save and Continue »] [Skip »]

Sidebar:
- Health Record Overview
- Basic Information
  - ▶ Registration Info
  - Identification
- Medications
- Conditions
- Allergies
- Additional Information
- Clinicians
- Immunizations
- Surgeries
- Specialty Modules
- Contact Info
- Employment Info
- Insurances
- Hospitals
- Pharmacies
- Healthcare Documents

Registration Information

*Required

User Information
User ID: Angel69

Patient Information
- Patient Name: Angela White
- Patient DOB: 11/11/1969  MM/DD/YYYY
- Patient SSN#: 123-45-6789  *--****
- Patient Gender: ○ Male ⊙ Female
- Patient Address 1: 649 Mission Street
- Patient Address 2:
- Patient City: San Francisco
- Patient State/Province: CA
- Patient Country: United States
- Patient Zip/Postal Code: 94105

Callout: Patients data is pre-populated from information already provided by the patient when they first registered on their doctors web site. Physician offices can also pre-populate these fields manually or through an interface with an existing EHR

| PATIENT INFORMATION | | | | Report created on 7/29/2005 | |
|---|---|---|---|---|---|
| NAME OF PATIENT (Last, First, middle) Washinton, George | | | SOCIAL SECURITY # 555-55-5555 | | |
| ADDRESS 649 Mission Street #200 | | | DATE OF BIRTH 11/11/1111 | | GENDER Male |
| CITY San Francisco | STATE CA | ZIP CODE 94105 | MARITAL STATUS Married | | # OF CHILDREN 2 |
| HOME PHONE 415-555-1212 | | | EMAIL george@washington.com | | |
| EMERGENCY CONTACT (EC) Franklin, Ben | | | EMPLOYER Medem, Inc. | | OCCUPATION President |
| (EC) ADDRESS | | | INSURANCE BCBS of CA Group # 123456 ID# AB987654 | | |
| (EC) CITY | (EC) STATE | (EC) ZIP CODE | | | |
| (EC) DAY PHONE | (EC) EVE PHONE | | | | |
| (EC) CELL PHONE | (EC) RELATION TO PATIENT | | | | |

Common Conditions

- ☐ Abdominal Pain
- ☐ ADHD/ADD
- ☐ AIDS/HIV Positive
- ☐ Alcoholism
- ☐ Alzheimer's Disease
- ☐ Anemic
- ☐ Angina
- ☐ Arthritis
- ☑ Asthma (Onset Yr 1989)
- ☐ Atherosclerosis
- ☐ Athlete's Foot
- ☐ Bladder/Kidney Infections
- ☐ Blood Clotting Disorder
- ☐ Breast Lumps
- ☐ Bronchitis
- ☐ Bursitis
- ☐ Carpel Tunnel Syndrome
- ☐ Cateracts
- ☐ Cellulitis
- ☐ Chickenpox
- ☐ Chlamydia
- ☐ Chronic Constipation
- ☐ Chronic Obstructive Pulmonary Disease
- ☐ Chronic Pain
- ☐ Colitis
- ☐ Colon Polyps
- ☐ Congestive Heart Failure
- ☐ Coronary Artery Disease
- ☐ Herpes
- ☑ High Blood Cholesterol (Onset Yr 1999)
- ☑ High Blood Pressure (Onset Yr 2002)
- ☐ High Lipids
- ☐ Hives
- ☐ Hypoglycomia
- ☐ Hypothyroidism
- ☐ Incontinenca
- ☐ Infertility
- ☐ Irritable Bowel Syndrome
- ☐ Jeundice
- ☐ Kidney Disease
- ☐ Kidney Failure
- ☐ Limb Pain
- ☐ Liver Problems
- ☐ Low Back Pain
- ☐ Low Blood Pressure
- ☐ Lupus
- ☐ Measles
- ☐ Meningitis
- ☐ Mental Health/Psychiatric Disorder
- ☐ Mental Retardation
- ☐ Migraine Headache
- ☐ Multiple Sclerosis
- ☐ Mumps
- ☐ Muscle Disorder
- ☐ Open Wounds
- ☐ Osteoarthritis
- ☐ Osteoperosis
- ☐ Strep Throat
- ☐ Stroke
- ☐ Syphilis
- ☐ Thyroid Problems
- ☐ Tonsillitis
- ☐ Tuberculosis
- ☐ Tumer
- ☐ Upper Resiratory Infection
- ☐ Urinary Tract Infections
- ☐ Varicose Veins
- ☐ Warts Cancers:
- ☐ Breast
- ☐ Colon/Rectum
- ☐ Leukemia
- ☐ Lung
- ☐ Non Hodgkin Lymphoma
- ☐ Ovary
- ☐ Prostrate
- ☐ Skin
- ☐ Urinary/Bladder
- ☐ Uterus
- ☐ Other Females Only:
- ☐ Abnormal PAP
- ☐ Bleeding problems
- ☐ Breast Mass or Cyst
- ☐ Contraception

| FIG. 10A |
|---|
| FIG. 10B |

KEY TO FIG. 10

| | |
|---|---|
| ☐ Crohn's Disease<br>☐ Depression<br>☐ Diabetes Type 1<br>☐ Diabetes Type 2<br>☐ Diarrhea<br>☐ Dizziness<br>☐ Drug Dependency<br>☐ Ear Infection<br>☐ Eczema and Psoriesis<br>☐ Emphysema<br>☐ Epilepsy<br>☐ Eye Problem<br>☐ Fainting<br>☐ Fibromyalgia<br>☐ Gastritis<br>☐ Gastroesophegeal reflux disease<br>☐ Genital Warts<br>☐ Glaucoma<br>☐ Gonorrhea<br>☐ Gout<br>☐ Hay Fever/Sinus Problem<br>☐ Hearing Impairment<br>☐ Heart Condition/Heart Disease<br>☐ Hemodialysis<br>☐ Hemorrhoids<br>☐ Hepatitis<br>☐ Hernis | ☐ Pain or Pressure in Chest<br>☐ Palpitations<br>☐ Paralysis<br>☐ Parkinson's Disease<br>☐ Peptic Ulcer Disease<br>☐ Periods of Unconsciousness<br>☐ Pertussis/Whooping Cough<br>☐ Phlebitis<br>☐ Pneumonia<br>☐ Polio<br>☐ Pulmonary Embolism<br>☐ Rash<br>☐ Rectal Bleeding<br>☐ Rheumatic Fever<br>☐ Rheumatism<br>☐ Rubella<br>☐ Scabies<br>☐ Scarlet Fever<br>☐ Seizures/Seizure Disorder<br>☐ Sexual Dysfunction<br>☐ Shingles<br>☐ Shortness of Breath<br>☐ Sickle Cell<br>☐ Sinus Infection<br>☐ Skin Lesien<br>☐ Smoking<br>☐ Stomach or Intestinal Problems | ☐ Cyst or abscess of vulve<br>☐ Discomfort with sex<br>☐ Endometriesis<br>☐ Fibroids<br>☐ Irregular Periods<br>☐ Menopause<br>☐ Miscarriage<br>☐ Nipple discharge<br>☐ Ovarian Cysts<br>☐ Pelvic Inflammatory Disease<br>☐ Postmenopausal bleeding<br>☐ Postpartum Depression<br>☐ Pregnancy<br>☐ Toxemia<br>☐ Tubal Pregnancy<br><br>Males only:<br>☐ Prostrate Problems<br><br>Others:<br>☑ Muscular Degeneration (Onset Yr 1999)<br>☑ Pink Eye (Onset Yr 2002) |

IMMUNIZATIONS: (Includes year of last vaccine)

Immunizations:
☑ Chickenpox (1974)   ☐ Polio
☐ Diphtheria          ☐ Rubella
☐ Hepatitis A         ☐ Smallpox
☐ Hepatitis B         ☐ Tetanus
☑ Influenza (2003)    ☐ Tuberculosis
☐ Measles             ☐ Typhoid
☐ Mumps               Combination Vaccines:
☐ Pertussis/Whooping Cough    ☐ Diphtheria/Tetanus/Pertussis
☐ Pneumococcal conjugate vaccine    ☐ Measles/Mumps/Rubella
☐ Pneumococcal polysaccharide vaccine    ☐ Tetanus and Diphtheria booster CURRENT MEDICATIONS: (Includes non-prescription products)

(Drug name – dose/frequency)
Medication Name – 800mg/Every 4hours
Medication Name – 800mg/Every 4hours
Medication Name – 800mg/Every 4hours
Medication Name – 800mg/Every 4hours ALLERGIES: (includes drugs, food, insects etc.)

(Allergy name – type of reactions)
Allergy Name – Reaction, reaction, reaction
Allergy Name – Reaction, reaction, reaction
Allergy Name – Reaction, reaction, reaction

SURGERIES AND PROCEDURES (Year – Procedure)
2005 – Surgery Name

NOTE: HAND TO THE DOCTOR OR NURSE, OR IF MAILED MARK ENVELOPE "TO BE OPENED BY MEDICAL OFFICER ONLY."

PRINTED NAME OF PATIENT: George Washington    SIGNATURE    DATE: 07/29/2005

This personal health record is powered by www.iHealthRecord.org

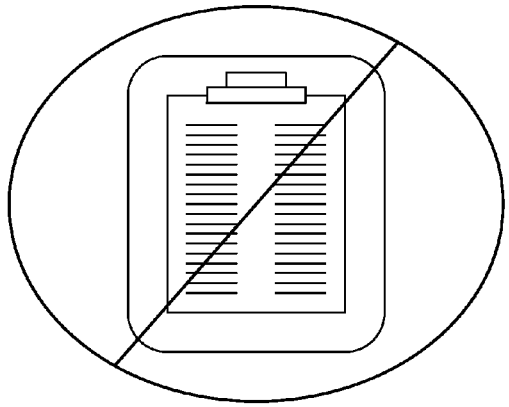

SHARP

iHealthRecord
In Partnership with America's Physicians

We know who you are...
You're our cherished patients! And service to you is very important to us. Our iHealth service means an end to "clipboard care." This secure personal health record will protect you and your family 24x7 and will travel with you wherever you go...'forever! Build your family's iHealthRecord online today, then simply print it and bring it with you on your next office visit 'And say goobye to the clipboard!
www.dickey.yourmd.com

FIG. 11

ELECTRONIC PERSONAL HEALTH RECORD SYSTEM

RELATED APPLICATIONS

This application is a continuation-in-part of application Ser. No. 11/085,984, entitled "ELECTRONIC PERSONAL HEALTH RECORD SYSTEM," listing Fotsch et al. as inventors, filed on Mar. 21, 2005, which is a continuation-in-part of application Ser. No. 10/387,041, entitled "HEALTHCARE PROVIDER-PATIENT ONLINE CONSULTATION SYSTEM," listing Fotsch et al. as inventors, filed on Mar. 10, 2003, and is a continuation-in-part of application Ser. No. 10/641,982, entitled "HEALTHCARE PROVIDER-PATIENT ONLINE CONSULTATION AND COMPLIANCE PROGRAM," listing Fotsch as inventors, filed on Aug. 15, 2003.

BACKGROUND OF THE INVENTION

1. Field of the Invention

The present invention relates to an electronic health record system. More particularly, the present invention relates to communications supporting the sharing of patient information in electronic health records.

2. Description of the Related Art

While the medical community has benefited from technological advances in the areas of medical devices and equipment, the medical community has lagged behind other businesses in the area of storing and integrating information electronically. One area where this is particularly problematic is in patient medical records.

Patient medical information and records are largely paper-based, particularly in the outpatient environment where most care is delivered. This paper process begins with healthcare providers collecting medical history and other relevant healthcare information from patients on paper, via the registration forms provided to patients on the "clipboard" when the patient presents for care. In addition to being paper-based, this method of collection often results in inaccurate and incomplete information because the patient (or caregiver) does not have access to the information required to accurately complete the registration form, they are typically distracted in the waiting room environment, and they are often hurried through this process.

In addition, particularly in the outpatient environment, patients often see a variety of physicians for their various medical needs. Unfortunately, this often requires medical records to be physically transferred among these physicians. This transfer generally requires effort on behalf of the patient and physician to request the record transfer. Moreover, in order to accomplish the record transfer, this generally requires processing time, as well as the time it takes for the physical medical file(s) to be transferred from one physician's office to another physician's office. This transfer time, delay, and resultant incomplete medical record is problematic for all types of care, and particularly problematic in the situation in which a medical emergency arises.

Simply capturing medical information electronically doesn't solve this problem. In those (few) physician offices and other care arenas where patient medical information is captured and stored electronically, the information stored is unique to the care provided by that institution, and the system limits access to those physicians and other healthcare providers operating within that office or institution. In this case, when records need to be transferred or accessed by a physician or other healthcare provider outside the system, the institution reverts back to a paper-based process of printing and transferring patient information as outlined above.

The lack of an electronic patient-centric medical record leads to astounding results. Approximately 20 percent of medical tests are ordered a second time simply because previous results cannot be located. Moreover, research indicates that 30 cents of every dollar spent on health care does nothing to make sick people better. Duplicate tests, unnecessary hospitalizations and other side effects contribute to skyrocketing healthcare costs.

Even if the majority of physician offices and other institutions had electronic medical records, the challenges associated with system-to-system integration of electronically stored patient medical information to create a comprehensive, patient-centric health record are significant. Among the most formidable of tasks is the creation of a unique patient identifier, or master person index, that would allow for the accurate integration of patient information into a single repository.

Moreover, physicians are being challenged to become more engaged in disease management. Payers, employers and other organizations are looking to technology to provide physicians with tools that can facilitate communication with and care for patients, to help patients do a better job of managing conditions/diseases and thereby reduce overall costs. In addition, as patients become more aware of the challenges associated with the current healthcare delivery system, and as they are increasingly forced to bear more of the financial burden associated with their healthcare costs, they are taking a more proactive role in the management of their health.

In view of the above, it would be very beneficial if improved systems for implementing electronic health records could be established.

SUMMARY OF THE INVENTION

Methods and apparatus for providing access to information associated with a patient are disclosed. For instance, patient information obtained from an electronic health record may be provided or transmitted (e.g., in paper or electronic form), thereby enabling such information to be shared among various entities interested in such information. In this manner, information from various electronic health records associated with a particular patient may be made available to entities such as the patient and/or healthcare provider.

In accordance with one aspect of the invention, the disclosed embodiments make patient personal health records available to patients (or caregivers) and other individuals such as healthcare providers on the Internet in a secure manner. For instance, a healthcare provider may be a healthcare provider authorized to practice medicine, such as a physician, nurse, physician's assistant, or nurse-practitioner. Other examples include chiropractors, optometrists, and dentists. In addition, healthcare providers may include service providers, such as pharmacists and lab technicians, who provide services to primary healthcare providers such as physicians. A healthcare provider such as a physician's assistant need not be capable of practicing independently. Rather, they merely need to be subservient to a healthcare provider (e.g., physician) and working within the healthcare provider's practice group, where the healthcare provider is associated with the healthcare provider network. Thus, the healthcare provider may be obtaining patient information from the patient's personal health record on behalf of a physician in conjunction with care being provided by a physician or other provider.

In accordance with another aspect of the invention, a patient (or caregiver) may grant access to a portion of the health record (or the entire health record). For instance, the patient may wish to permit access to merely a portion of the health record in order to protecting confidential and sensitive information, such as HIV status or breast implants.

In accordance with another aspect of the invention, a patient (or the patient's caregiver) may choose to either grant or deny access rights to an individual such as a healthcare provider. The patient may decide whether to grant permission to access at least a portion of the electronic personal health record associated with the patient to one or more individuals. Access rights that may be granted (or denied) via the health record permission grant may include read, write (e.g., including delete), and/or forwarding privileges. Even where a patient or caregiver has not granted access rights to a particular healthcare provider (or has specifically denied access rights to the healthcare provider), this state may be overridden in emergency situations, in accordance with one embodiment.

In accordance with yet another aspect of the invention, any access rights that have been granted (or denied) by the patient or caregiver may subsequently be revoked. Specifically, a patient may revoke the permission that was previously granted to at least one of the individuals. Again, the revocation may pertain to a portion of the health record or the entire health record.

In accordance with yet another aspect of the invention, once a third party such as a healthcare provider is granted access rights, those access rights may be granted to another individual, such as another healthcare provider. In accordance with one embodiment, only those access rights that have been granted to the original individual may be granted to another individual by the "grantee." For instance, if a healthcare provider has only been granted read access, that healthcare provider may only grant read access rights to another individual. The "grantee" may also choose to revoke these rights at a later date. In accordance with one embodiment, the patient (or caregiver) is notified of any additional access rights provided to additional individuals by a "grantee."

In accordance with yet another aspect of the invention, an electronic personal health record may be generated and/or updated by a patient (or caregiver), as well as a healthcare provider, payor or other organization providing care for or otherwise involved in the provision of healthcare. In accordance with one embodiment, when individuals or entities other than the patient or caregiver make information available for updating the electronic personal health record, the patient may accept or decline all or portions of the information. Thus, such entities need not have write access to the patient's health record. In order track the changes to the health record, an auditing trail may be maintained. For instance, the organization or person modifying the health record may be identified, as well as the change made by that person and the date and time that the change was made. In this manner, the patient may track changes made to the health record, accept or reject any addition or changes to the health record, as well as make corrections, as necessary.

In accordance with another aspect of the invention, information obtained from a patient's electronic personal health record can be provided to a healthcare provider. Since this information may replace a manual intake registration form that is typically filled out by patients visiting a healthcare provider, this can eliminate the need for the patient (or caregiver) to fill out a manual intake registration form associated with the healthcare provider. Such information can be printed out or transferred to an electronic medical record maintained by the healthcare provider. Thus, such information can serve as the registration required before care can be provided by the healthcare provider. For instance, the patient can print the personal health record, sign it, and provide it to the provider office upon arrival. In another example, automated transfer of the data can occur between the patient's electronic personal health record and the office/institution electronic medical record, thereby making the information available to the provider electronically. In this case, the provider can, if they wish, print the health record information for review with the patient upon arrival. This information may thereafter be used to update (or create) the patient's medical record (e.g., paper or electronic) maintained by the healthcare provider.

In accordance with yet another aspect of the invention, information from an electronic personal health record (e.g., online health record controlled by a patient) or a portion thereof may be provided electronically to an entity such as a healthcare provider. Specifically, patient records may be maintained and controlled by multiple entities, such as healthcare providers, patients, payors, or other third parties. Information from these records may be transferred among these entities, thereby enabling updates to such records to be performed. For instance, a patient-controlled electronic personal health record may be updated with information obtained from an electronic health record maintained by a healthcare provider or payor. As another example, a healthcare provider maintained electronic medical record may be updated (or created) with information obtained from the patient-controlled electronic personal health record or an electronic health record controlled by a third party (e.g., payor). These updates may be transmitted automatically, upon initiation by a user (e.g., patient, healthcare provider, or payor), or may be triggered by various events such as the discharge of a patient from the care of a healthcare provider. In addition, such updates may be stored automatically or upon acceptance by the receiving entity (e.g., patient or healthcare provider). Specifically, such updates may be accepted or rejected implicitly or explicitly by the receiving entity (e.g., patient or healthcare provider), in whole or in part, prior to storing such updates.

In accordance with one embodiment of the invention, the electronic personal health record may serve as the gateway or point of entry (e.g., via a link) to third party provider databases containing detailed medical information on the patient. These provider databases include, but are not limited, to hospitals, medical centers, labs, etc.

In accordance with yet another aspect of the invention, compliance programs may be initiated based upon medical conditions (e.g., allergies) or medications identified in the health record. A compliance program enables a sequence of electronic messages to be transmitted electronically to the patient (or caregiver) that is relevant to the medical condition (s) and/or medication(s) identified in the health record. In this manner, the patient (or caregiver) may receive information that is considered pertinent to the health of the patient.

These and other features of the present invention will be described in more detail below in the detailed description of the invention and in conjunction with the following figures.

BRIEF DESCRIPTION OF THE DRAWINGS

FIG. 4 is an exemplary graphical user interface enabling a patient to submit registration information.

FIG. 9 is an exemplary graphical user interface enabling a patient or other individual to view or print the patient's electronic personal health record or portion thereof.

FIG. 10 is an exemplary printout representing the electronic personal health record registration that replaces the medical office clipboard-based registration process.

FIG. 11 is an exemplary graphic of the medical office promotion of the electronic personal health record representing no more clipboards.

DETAILED DESCRIPTION OF THE INVENTION

In the following description, numerous specific details are set forth in order to provide a thorough understanding of the present invention. It will be obvious, however, to one skilled in the art, that the present invention may be practiced without some or all of these specific details. In other instances, well-known process steps have not been described in detail in order not to unnecessarily obscure the present invention.

Various embodiments of the present invention support the storing, updating, accessing, and forwarding of electronic personal health records. By providing the patient (or caregiver) control over who has access to his or her personal health records, the patient may grant or deny access to their electronic personal health record to a particular individual, who may be a healthcare provider or other third-party. In this example, the healthcare provider is a physician, but the healthcare provider may merely be an individual who works in the healthcare industry, an individual who is merely associated with a physician, or an individual who provides care for the individual.

The terms user and patient will be used interchangeably herein. However, it is important to note that a user need not be a pre-existing patient of a physician in order to grant or deny access by the physician to the patient's personal health records.

Figure 1:
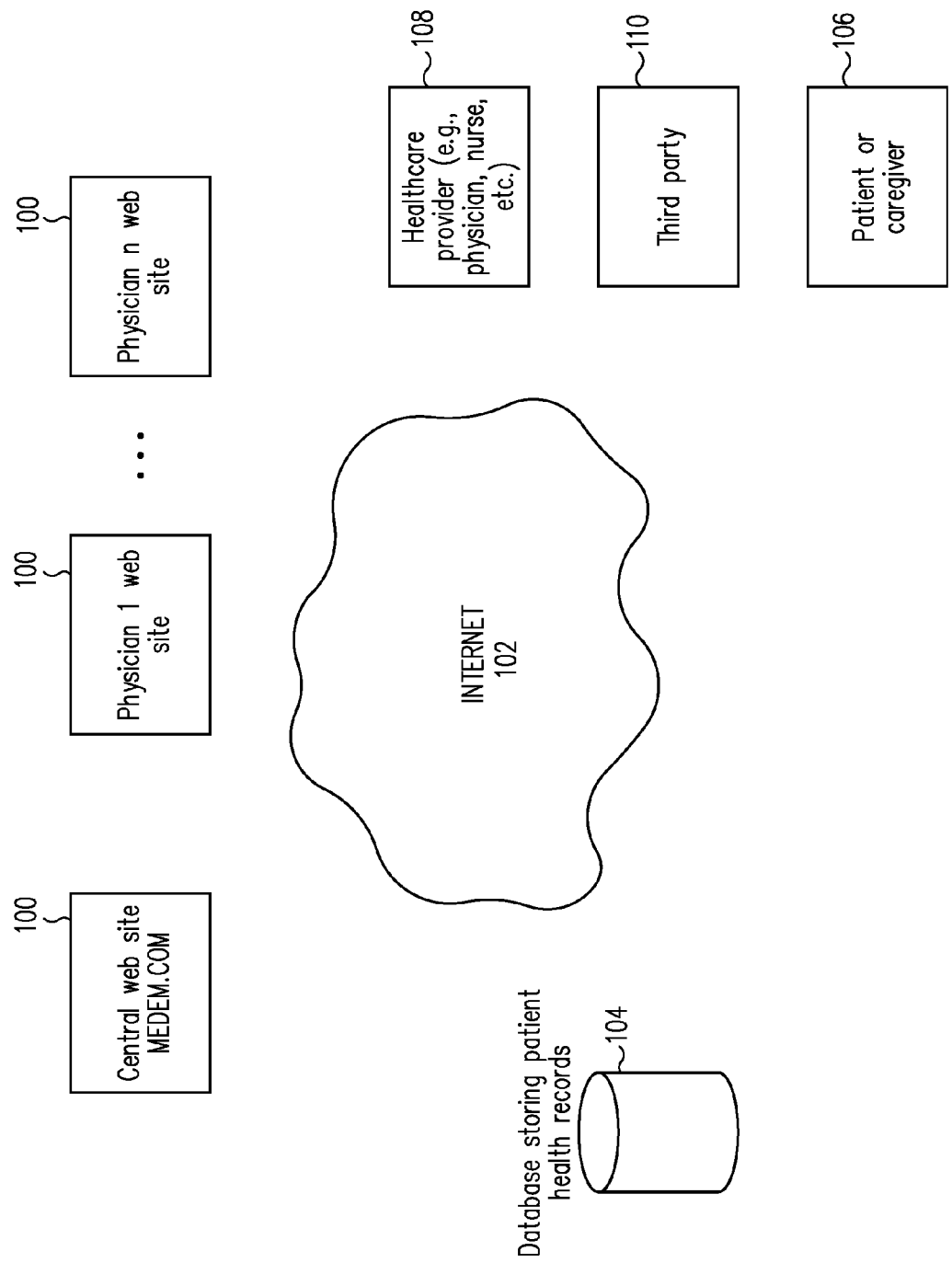
FIG. 1 is a block diagram illustrating one embodiment of a system in which the present invention may be implemented.

FIG. 1 is a block diagram illustrating one embodiment of a system in which the present invention may be implemented. In accordance with various embodiments, physicians may access personal health records of patients via a web site 100 via the Internet 102. For instance, the web site 100 may be a web site that is associated with the physician. This physician may also offer online consultation services via this web site 100 as disclosed in patent application Ser. No. 10/387,041, entitled "HEALTHCARE PROVIDER-PATIENT ONLINE CONSULTATION SYSTEM." Moreover, the physician may initiate a compliance program on behalf of a patient as disclosed in patent application Ser. No. 10/641,982, entitled "HEALTHCARE PROVIDER-PATIENT ONLINE CONSULTATION AND COMPLIANCE PROGRAM," enabling the patient to receive messages that are pertinent to a particular medication or medical condition.

Through a third-party service, a plurality of physician web sites 100 may be supported. Through the physician's "practice view" or single point of access, the physician may access practice information, health plan hypertext links and services, medical education services, medical supplies and practice services, secure messaging services and/or compliance programs. In addition, the physician may access a patient's personal health records, which may be stored in a database 104, as set forth in further detail below.

In accordance with one embodiment, the patient controls access to his or her medical records. For this purpose, multiple types of messages are available to the user, including what may be referred to as a "health record permission grant" via which a user (e.g., patient or caregiver) 106 may grant access to his or her personal health records to a healthcare provider 108 or other third-party 110 and a "health record permission revocation" which the user may use to revoke any access privileges that have been previously granted to a particular individual, as will be set forth in further detail below.

Secure messaging may enable a physician and a user (e.g., patient) to communicate with one another for a variety of reasons. For this purpose, various types of messages may be available. For instance, a notification of health record access may enable a user 106 to notify a healthcare provider 108 of access to his or her medical records. Similarly, the user 106 may choose to notify the healthcare provider 108 when these access privileges are revoked.

In other embodiments, physicians need not have a web site in order to access a patient's personal health records. Rather, a physician may access a patient's personal health records via a central web site such as ihealthrecord.org.

In accordance with one embodiment, the electronic personal health record services are supported by a third-party service that receives a specified fee for this service. For instance, the third-party service may receive a monthly or annual subscription fee from a physician (or patient), or insurance company.

In accordance with one embodiment, electronic personal health record services are accessed via secure messaging. For instance, secure messaging may be accessed via a personal mailbox established for the physician and the patient. By logging in and entering a password, messages in the personal mailbox may be accessed. Non-confidential e-mail messages may be sent electronically to the physician or patient indicating that a confidential message is waiting to be retrieved from the personal mailbox.

The physician may choose message access levels for other practice members associated with the physician. For instance, the physician may wish different members of his or her practice to have varying levels of access to patient information such as electronic personal health records, as well as patient online messages such as registration, appointment request, appointment reminder, prescription renewal, and/or online consultation messages, including those received and transmitted by the physician. Thus, the physician may select a message access level indicating a level of access to electronic personal health records or messages including online consultation messages for various practice members. In this example, the level of access may be full, partial, or none. The level of access indicates whether the individual has read, write, reply, forwarding and/or delete control access. Full access allows the practice member(s) complete access to the mailbox and setup pages, including read, write, reply, forwarding and delete control access. Partial access enables the physician to enable a practice member to have limited access to physician-patient online messages. For instance, the physician may choose to enable read, write, reply, forwarding and/or delete control access for a particular practice member. In addition, the control access selection may be further designated for each message type, as well as separately for electronic personal health record access. The physician may further provide message text that will be sent to patients via their email address to alert them when a message is waiting from the physician at the physician's website.

A practice member may be assigned a message access level indicating a level of access (e.g., full, partial, or none). Partial access may indicate, for example, read, reply, and forwarding access, but not write or delete access. In this example, the message access level is further associated with the type of message or service (e.g., electronic personal health record access). Thus, the practice member is actually assigned multiple access levels corresponding to the multiple message or service types. Exemplary message types include electronic personal health record permission grant or revocation, online consultation, registration request, general message, refill request, and appointment request.

Figure 2:
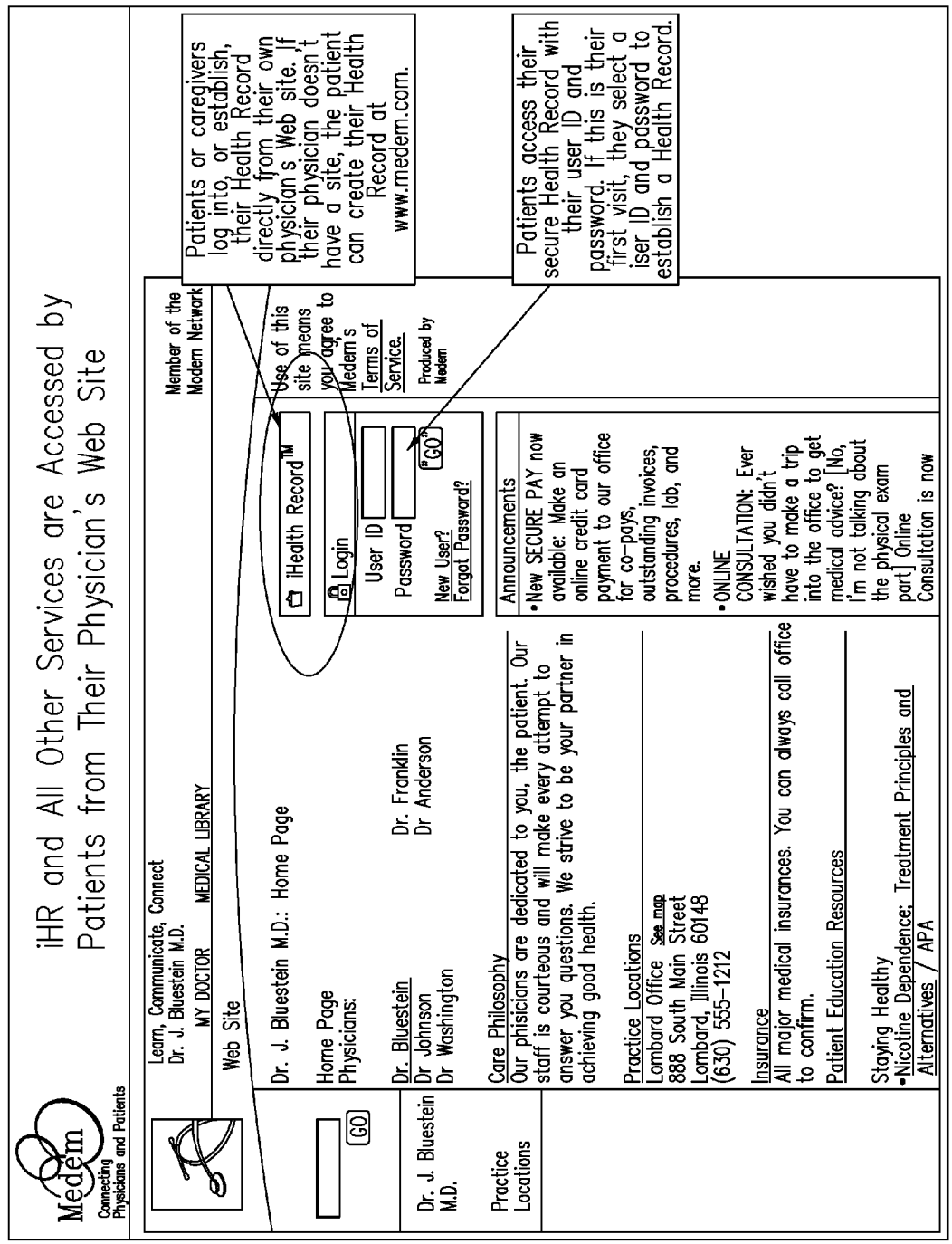
FIG. 2 is an exemplary graphical user interface enabling a patient to access or generate an electronic personal health record.

In order to submit or update his or her personal health record, a patient may access a physician's web site or, alternatively, a central web site (e.g., if the physician does not have a web site). FIG. 2 is an exemplary graphical user interface enabling a patient to access or generate an electronic personal health record. In this example, the patient gains secure access to the physician's web site via a user ID and password. If this is their first visit, the patient may select a user ID and password to establish a health record.

Figure 3:
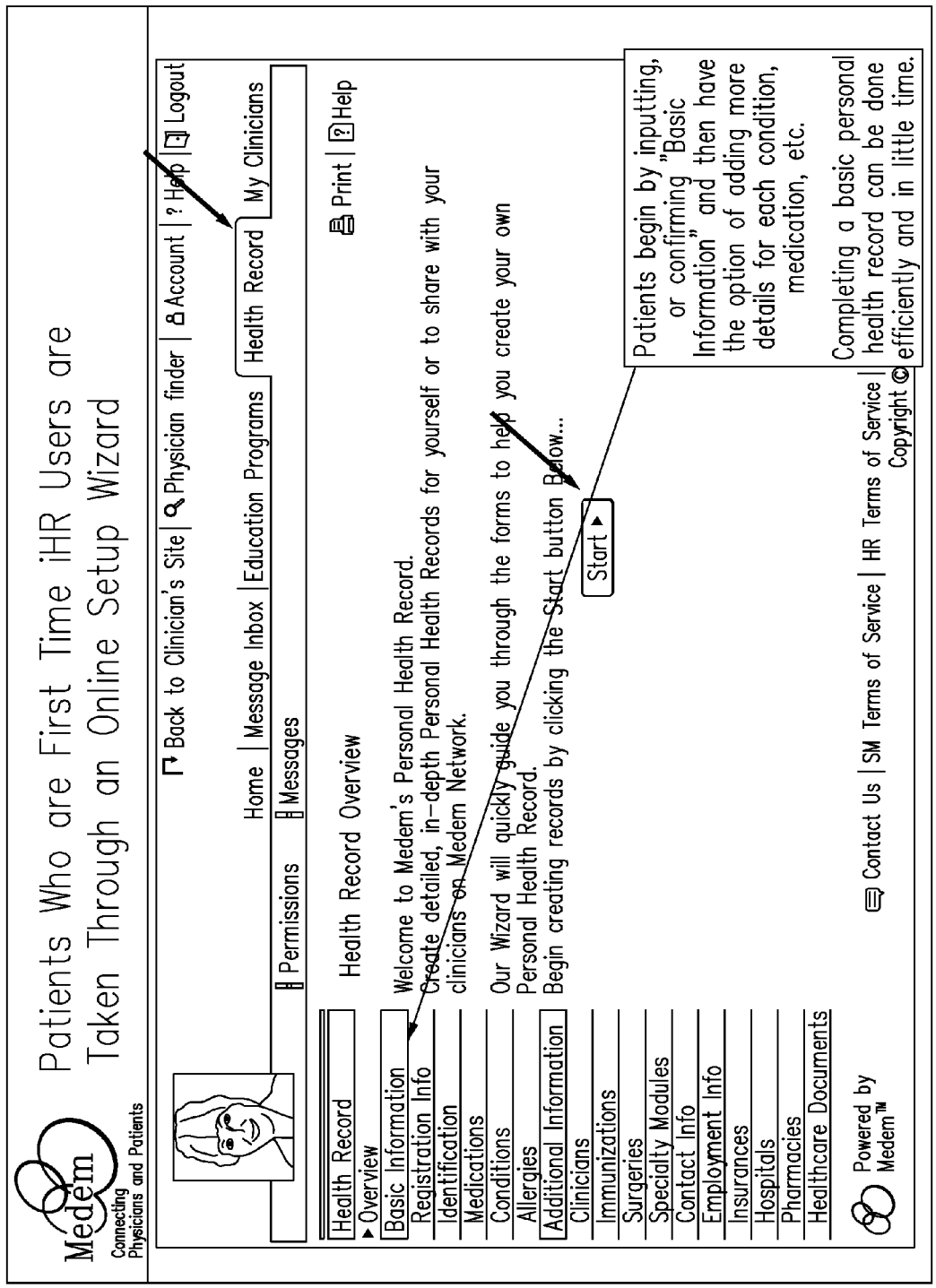
FIG. 3 is an exemplary graphical user interface enabling a patient to input or update the patient's personal health record.

FIG. 3 is an exemplary graphical user interface enabling a patient to input or update the patient's personal health record. In accordance with one embodiment, the user is guided through the health record generation process by clicking the "Start" button. They first enter basic information, and have the option of adding more details for each medication and medical condition/allergy. In this manner, a patient (or patient's caregiver) may input or update a patient's personal health record via a physician's web site.

The electronic personal health record may include basic information such as insurance information (where applicable) and employment information. In addition, the electronic personal health record may include information that may be pertinent to the medical history of the patient such as immunization history, surgical history, family medical history, lifestyle information, health risks (e.g., sexual encounters), vital signs, test or lab results, imaging results (e.g., x-rays), and a "review of systems" indicating a review of the patient's systems by a healthcare provider. The electronic personal health record may also include registry information indicating implantable devices or diseases pertinent to the patient. The electronic personal health record may also include or contain links to legal documentation (e.g., release of liability), secure messages and online communications, long term care information, insurance or care plans, nutrition support indicating the types of nutrition support (e.g., supplements) that the patient may need for a particular condition, and information entered via a specialty module for a disease state or health state. For instance, a specialty module may be designed to enable a patient to upload or enter information that is specific to a particular disease state or health state. As one example, a module for diabetes may enable a patient to upload or enter glucose results, food intake, exercise, etc. As another example, a pediatrics module may enable growth and development to be tracked, while a geriatrics module may enable information related to hypertension to be tracked, etc. In addition, special clinical information related to the patient's health, such as diabetes, asthma, cardiac health, etc., may also be captured in the electronic personal health record. The electronic personal health record may also include or contain links to third party systems such as healthcare provider or payor maintained systems where additional clinical details or other information associated with the patient can be found. Other information provided in the health record may include contact information such as emergency contact information, caregiver contact information, and physician information identifying one or more physicians of the patient. The patient may also choose to specify his or her preferences, such as at least one preferred pharmacy and/or at least one preferred hospital. Moreover, a photograph of the patient may also be uploaded and associated with the electronic personal health record.

In accordance with one embodiment, the patient submits basic information via a registration process. In accordance with an alternative embodiment, the patient must register with the physician's web site in order to input or update a personal health record via the physician's web site. Thus, if the user has not yet registered with the physician's web site, the user may go through the registration process in order to submit or update his or her personal health record via the physician's web site. In accordance with one embodiment, the user may click on the "Log In" hypertext link to log in, or the "New User" hypertext link in order to register with the physician's web site as a new user. In accordance with the described embodiment, registration is performed to request permission to send and receive messages from a physician via the Internet, as well as submit or update his or her electronic personal health record.

Via the registration process, a patient may obtain access to services enabled by the physician's web site, such as online consultation, secure messaging services and/or compliance programs. FIG. 4 is an exemplary graphical user interface enabling a patient to submit registration information. In accordance with one embodiment, the user may register by entering identifying information such as first and last name. In addition, an e-mail address may be entered in order to enable the patient to be notified of messages waiting for him or her at the physician's web site. For instance, the patient may receive notification of his or her registration or ability to send or receive secure messages. In addition, the patient may receive notification that an online consultation reply message is waiting to be read by the user. Confidential health and medical information and advice may then be accessed via the web site using a user ID and password configured during registration. In this manner, the present invention provides a secure and confidential mechanism for providing medical information via the Internet. In alternative embodiments, communications may also be sent via the standard, non-secure e-mail address.

Additional identifying information may also be entered. For instance, this information may be used by a physician to enable the physician to accurately identify the patient prior to providing medical advice. The information may include, for example, date of birth, social security number, gender, address, and phone number. A second e-mail address may also be provided. From the registration information, a registration message is sent to the physician.

From the physician's registrations in-box, the physician may access registration messages (i.e., online message privilege requests), as shown. In addition, the physician may access all notifications (e.g., notification of personal health record access permission, denial of access, or revocation of permission previously granted to the physician) via the physician's in-box. Each online message or notification may identify the sender/patient, the date sent, and the subject (e.g., grant, denial, or revocation of grant) of the message. The physician may choose to delete or save a particular message.

In accordance with one embodiment, the physician may accept or decline online message privilege requests. In this manner, the physician controls patient access to the network in which the physician's web site is a gateway. For instance, by opening a registration message, the physician may accept the registration or decline the registration. The physician may decline registration simply by deleting the registration request. Alternatively, the physician may accept the registration by sending an approval notification message. Once registration is approved and the user has been granted privileges for online messaging (e.g., online consultation or compliance messages), the user can send messages such as online consultation request messages to the physician, as well as receive messages such as online consultation reply messages from the physician. In alternative embodiments, registration is an automated process resulting in immediate approval of online registration messages. In addition, in accordance with one embodiment, the physician with whom the patient is registered automatically has access to the patient's health record.

In accordance with one embodiment, the physician receives at least a portion of the registration information supplied by the patient during registration. For instance, the registration message received may include identifying information for the user-patient. However, the message will not include confidential information such as userID and password.

The physician can also select one or more message types that the patient can send to the physician (or receive) via the Internet. As described above, these message types may include online consultation, appointment, prescription renewal, and general mail (e.g., administrative question related to the patient's personal health records). Thus, the physician may modify the default settings the physician previously set by indicating those message types that may be received from users on a per-patient basis.

In accordance with one embodiment, once a user has successfully registered via a physician's web site, the user may then send messages such as online consultation requests or messages related to the patient's personal health record to the physician via that web site. The physician may also send messages to the user, which the user may access using the previously established user ID and password. For instance, when the physician sends a message relating to the user's personal health records, the user may receive a message via his or her e-mail address. Specifically, in accordance with one embodiment, the user may be notified via his or her e-mail address when an online message has been sent to the user. Thus, the message received via the e-mail address may simply indicate that a message (e.g., a confidential message) can be retrieved by the user at the physician's web site by entering the username and password established during the registration process. When the user logs into the physician's web site, the confidential message may be retrieved by the user via the physician's web site. Alternatively, the entire message may be sent to the user's e-mail address.

For instance, in order to generate an online consultation request, a user may click on the "Online Consultation Request" hypertext link of the physician's web site in order to generate and transmit an online consultation request to a physician via the Internet. In this manner, the user may request medical information and/or medical advice within the space provided in the online consultation request form.

Upon submission of the online consultation request by the patient, the physician may access the online consultation requests via his or her online consultation in-box. Upon reading the online consultation request, the physician may either accept or decline the online consultation request. For instance, the physician may decline the online consultation request if he or she feels that there is not enough information to provide medical advice. Similarly, the physician may feel that the patient needs to be seen before a diagnosis or other medical information can be provided to the patient. If the physician chooses to accept the online consultation request message, the physician responds by sending an online consultation reply message. The physician may also choose to import information from the patient's electronic personal health record into the online consultation reply. The online consultation reply may be sent to the patient's in-box with a notification sent via the patient's e-mail address.

Figure 5:
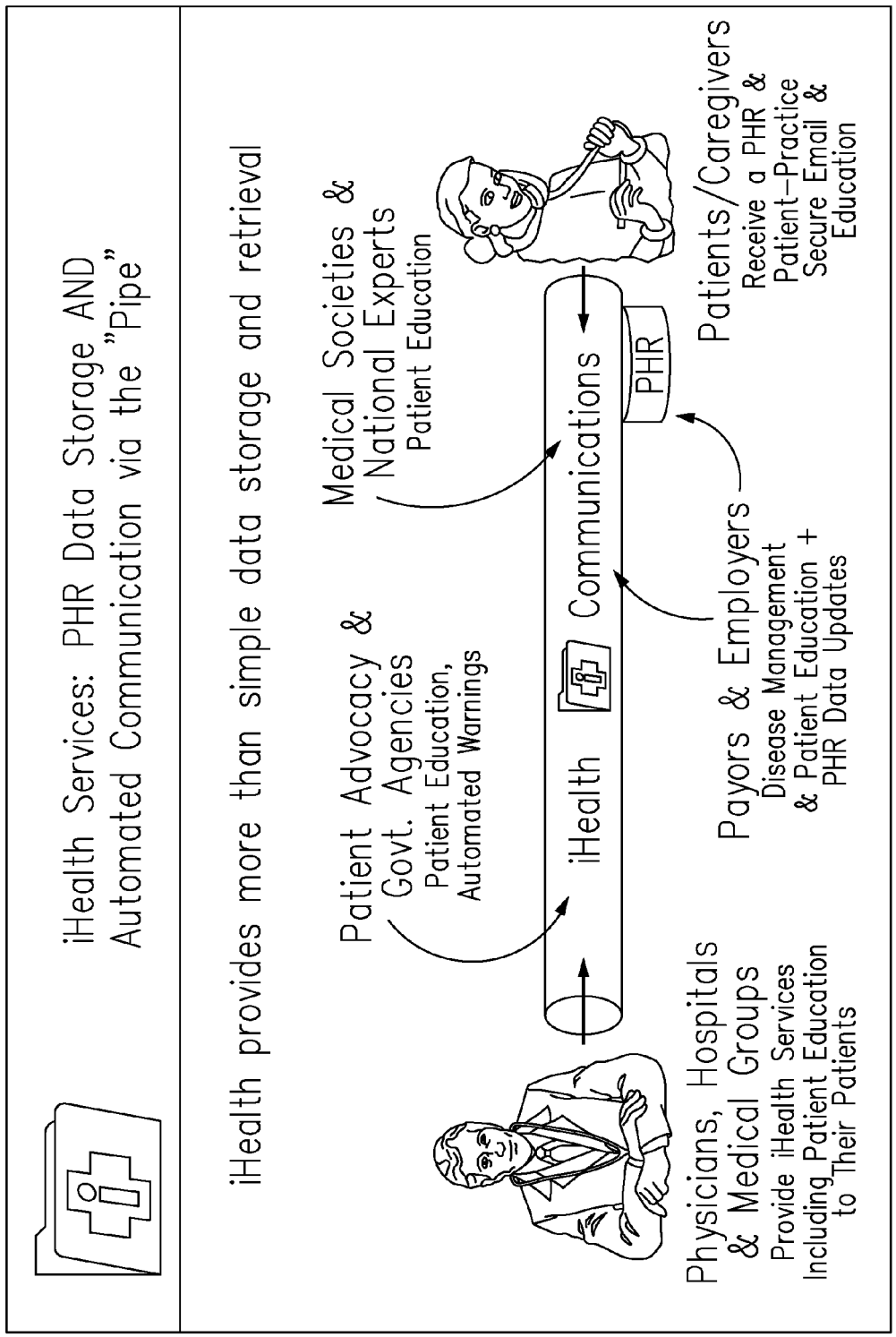
FIG. 5 is a diagram illustrating a communications pipe that is created between a provider and a patient through the establishment of an electronic personal health record that may be accessed by the provider, the patient, and other third parties interested in communication with the patient.

FIG. 5 is a diagram illustrating a "communications pipe" that may exist among patients and third parties such as healthcare providers and payors. In accordance with one embodiment, such a pipe may be generated as a result of the online registration process completed by the patient (or caretaker). In this simplified illustration, the communications pipe is shown as a single pipe. However, it is important to note that this example is merely illustrative, and communications and data may be transmitted among a variety of entities, such as those shown in FIG. 5. As shown, such entities include, but are not limited to, healthcare providers (e.g., physicians, hospitals, medical groups), patients or caregivers, and other third parties (e.g., payors, employers, patient advocacy and government agencies, medical societies and national experts). Such transmissions may be automated, as well as initiated by a user such as a patient or caregiver, healthcare provider, or payor. The data that is transmitted may be used to update a record associated with a patient such as an electronic personal health record controlled by the patient or an electronic medical record controlled by the healthcare provider. While it is possible to automatically update such a record, it is preferable to enable the patient or healthcare provider to accept or reject such updates to the electronic personal health record or electronic medical record, respectively.

Transmissions of data may also be triggered by various events, such as the discharge of a patient from the care of a particular healthcare provider. For instance, the patient may be discharged from hospital care. As another example, the patient may choose to leave one physician in favor of another physician. At this time, data stored in an electronic health record may be pushed to the electronic personal health record system maintained by the patient. For instance, when a patient chooses to leave the care of one physician, the data in the electronic medical record maintained by that physician may be transmitted for use in updating the patient-controlled electronic personal health record, and then made available to the newly chosen physician's office, either in paper form or via an update to the electronic medical record. In this manner, regulatory requirements of facilities such as hospitals requiring that patient information be provided upon discharge may be satisfied.

Records may be maintained in one or more databases for which the content may be controlled by various entities (e.g., patients, healthcare providers, payors, etc.), as well as be stored in a variety of storage mediums. For instance, a central system providing electronic personal record functionality to patients (and caregivers) may have one or more databases for storing electronic personal health records maintained and controlled by corresponding patients. Similarly, an electronic medical record system maintained and controlled by one or more healthcare providers (or an associated network) may have one or more databases for storing electronic medical records for one or more patients. Other third parties such as payors may have similar means for storing patient information such as clinical information or records of payment (or denial of payment).

Figure 6:
FIG. 6 is an exemplary graphical user interface enabling a patient to identify medications that the patient is taking.

In addition to the basic patient information, the patient may also include other information in the electronic personal health record, such as identify medications that he or she is taking. FIG. 6 is an exemplary graphical user interface enabling a patient to identify medications that the patient is taking. In this example, the patient may select medications from a pre-defined list (or drop-down menu). A subsequent screen may enable the patient to enter additional details associated with the selected medications. The same or similar format may be used to enter information for the patient's medical conditions and allergies.

Figure 14:
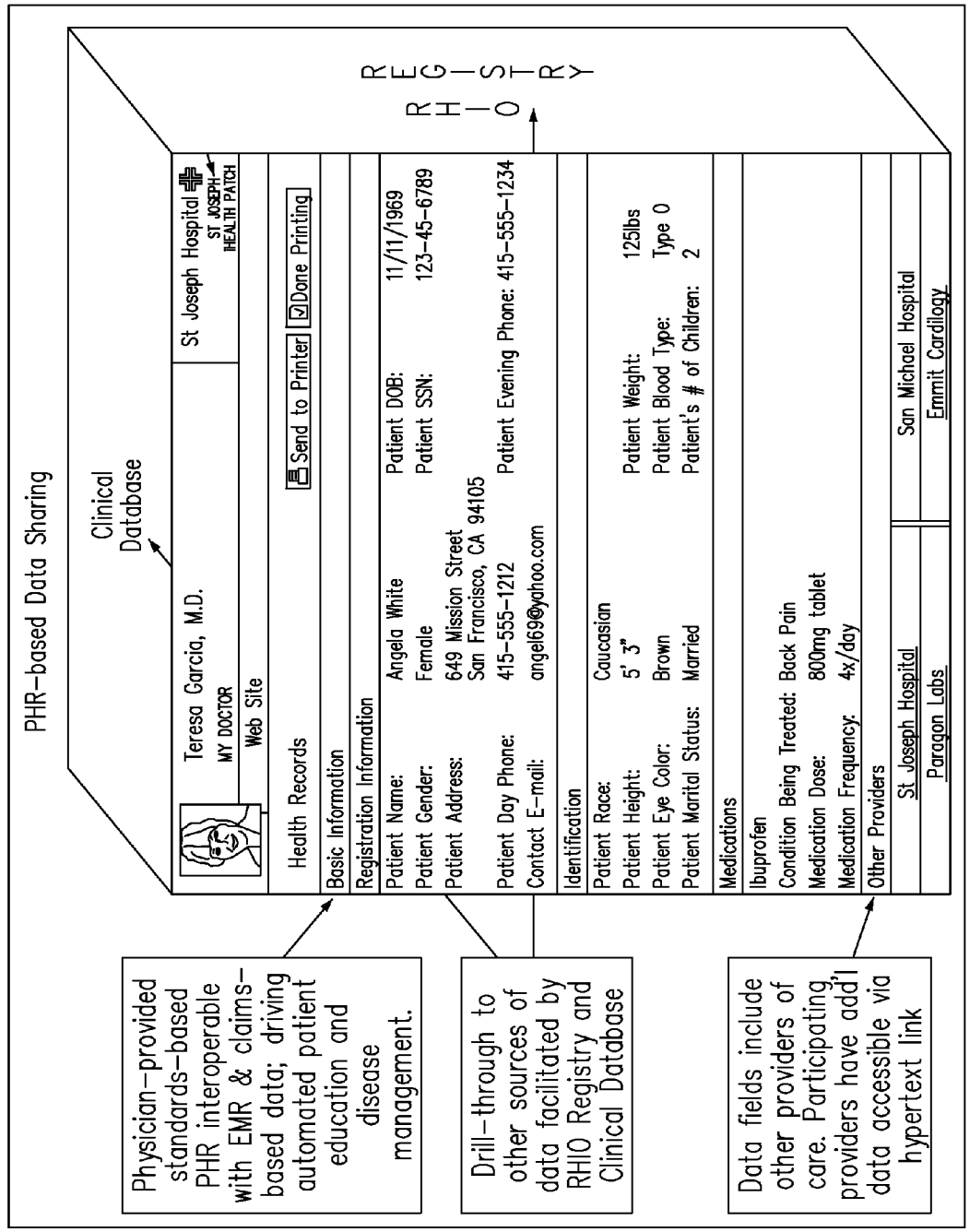
FIG. 14 is an exemplary graphic of the electronic personal health record containing links to third party provider systems containing more detailed clinical information on the patient.

As will be described in further detail below, FIG. 14 is an exemplary graphical user interface of the patients' view of third party data that has been sent to update the electronic personal health record, which can be used to update the electronic personal health record. In this example, the third party data is that of a healthcare provider. However, it is important to note that the third party need not be a healthcare provider. For instance, the third party may be a payor or other entity.

Information in the patient's electronic personal health record may be used to initiate or offer messaging programs that are pertinent to that particular patient. For instance, it may be desirable to send routine messages to patients in association with a medication that has been prescribed or a medical condition with which the patient has been diagnosed. These routine messages may be referred to as "compliance messages." A compliance message may be defined as a message that is sent to patients taking a specific drug or with a specific disease state. For instance, a prescription compliance message may be used to communicate information regarding a particular drug such as side-effects, refill-reminders, or other drug-related messages such as warnings or drug interaction or disease state. Thus, compliance messages messages may communicate medical advice or information such as side effects, refill reminders, etc.

Compliance messages may be stored as a group of messages to be sent sequentially, which will be referred to as a "compliance program." For instance, each of the messages may be sent when a specific condition has been satisfied, such as a lapse of time or in response to input from the user obtained in relation to a previously transmitted message. Input from the user in response to a message may determine the next message that will be transmitted to the user. Thus, the messages may be stored in a decision tree format as well as a list format, depending upon whether input is to be obtained from the user. Thus, automated compliance program messaging may be triggered by specific patient responses. User responses may be transmitted in the format of forms that both solicit patient input as well as provide structured information back to the physician.

Figure 7:
FIG. 7 is an exemplary graphical user interface enabling a patient to enter into an online compliance program.

In accordance with one embodiment, if a patient selects a medication or medical condition in their personal health record for which their physician (or central web site) offers an online education program (e.g., compliance program), the patient may be automatically enrolled in the program or may be prompted to enroll in the program. FIG. 7 is an exemplary graphical user interface enabling a patient to enter an online compliance program. The compliance program may be related to a medical condition or medication. In this example, the patient may be enrolled in one or more compliance programs associated with medical condition(s) or medication(s) indicated in their health record (e.g., for which the physician has enabled compliance programs). Compliance messages are then sent to the patient as scheduled in the compliance program.

It is also important to note that the messages may be sent to the patient as well as a user (e.g., caregiver) other than the patient, such as where the patient is a minor or incapable of communicating or caring for themselves (e.g., due to age, a handicap or senility). Thus, the user may be a relative (e.g., parent or sibling) or caretaker of a patient of the healthcare provider to which the compliance program is directed.

A plurality of compliance programs may be stored for access by a healthcare provider. Each compliance program may be generated locally (e.g., on a personal computer) or via the Internet. Each library of compliance programs may include compliance programs that are public as well as those that are private (e.g., a physician's personally edited compliance programs). Some of these compliance programs may be "send only" (e.g., read only) programs, which cannot be modified. Other compliance programs may be modifiable and therefore customizable by the healthcare provider. Specifically, each message in a compliance program may serve as a template which is customizable by the healthcare provider. These templates may be based, for instance, on a specialty of practice. Alternatively, a template may be "blank," enabling a healthcare provider to establish a compliance program "from scratch." In addition, the healthcare provider may choose to add a compliance program, delete a compliance program, or edit a specific compliance program. Editing a specific compliance program may, for example, include adding a message to the compliance program, deleting a message from the compliance program, rearranging messages within the compliance program, and/or editing the text of a message within the compliance program. The healthcare provider may also wish to append a note from the healthcare provider to one or more of the messages, such as where the compliance program or message is "send only." Alternatively, the healthcare provider may enter a URL, article, or text into one or more of the messages in the compliance program. In addition, the healthcare provider or generator of the message may choose to require the user to input a response to the message, which may be used to determine the next message in the compliance program to be transmitted to the user.

Each compliance program may be established to serve a particular purpose or particular population of patients. Thus, each program can be unique in terms of the content of the messages contained within (e.g., template), the number of messages, and the ability to set timing or delivery intervals (e.g., conditions) for the transmission of the messages. For instance, a compliance program may be associated with a new medication that has been prescribed or a new medical condition that has been diagnosed. As another example, a compliance program may be associated with a chronic (e.g., ongoing) medication or medical condition. Messages may be different for a new prescription compliance program and a prescription renewal compliance program. Any message in the compliance program may be a prescription renewal reminder in such a "chronic" compliance program. This renewal reminder may also enable the user to click a link within a compliance message to renew the prescription (if this link has been added to that message). Thus, the healthcare provider may have the ability to add or remove such a URL link from any compliance message.

In order to edit a compliance program by establishing the messages in the compliance program, it may also be desirable to define or alter the condition(s) associated with one or more of the messages in the compliance program. Specifically, the healthcare provider may define a condition such that a condition is associated with one or more of the messages that must be satisfied in order to trigger transmission of the corresponding message to the user. A condition may include various user and/or physician initiated events, as well as time factors.

The healthcare provider may choose to associate a specific compliance program with one or more users/patients, such as a set of one or more individuals who have been diagnosed with a particular medical condition or who have been prescribed a particular medication, or those individuals of a certain age or gender, which the healthcare provider may be able to see and/or select from the patients' personal health record. The healthcare provider may then view information associated with a specific compliance program, as well as the status of a particular executing compliance program for a particular user or set of users. The healthcare provider may also view a compliance program that is executing for all patients enrolled in that compliance program. The healthcare provider may, therefore, monitor the stage of execution of a compliance program.

A compliance program may be initiated by the electronic personal health record system wherein the patient is automatically enrolled in programs pertaining to the information contained within the electronic personal health record, by a healthcare provider, as well as by a user (e.g., patient), as set forth above. For instance, an online consultation may end in the healthcare provider option to initiate the compliance program for a medical condition. As another example, a prescription renewal application may end in the healthcare provider option to initiate the compliance program for the medication prescribed.

A compliance program, once initiated, is executed until completion unless disabled or cancelled by the user or healthcare provider. Each compliance program may include a set of messages which are executed by a set of computer-readable instructions. The set of computer-readable instructions may be associated with a compliance program, or serve as a stub that executes any compliance program in accordance with conditions/rules that have been established with the messages in the compliance program.

As described above, the healthcare provider may also choose to launch a compliance program from a library of compliance programs available to the healthcare provider. As shown, when a healthcare provider sends a message to the user, he may add URL links to the message. For instance, the URL links may be stored in a library available to the physician or healthcare provider. In addition, the healthcare provider may choose to launch a compliance program, such as through the checking of a box in association with a reply message (e.g., to an online consultation message).

From a compliance message, the user (e.g., patient) can renew a prescription or reply to the healthcare provider (e.g., physician). If the user replies, the user is given the choice of which type of secure message to send to the physician. For instance, the user may wish to send an online consultation request message, a prescription renewal request message, or an appointment request message.

The compliance program (e.g., template) may enable a healthcare provider to create an adverse reaction functionality. Specifically, if a patient has an adverse reaction to a medication that has been prescribed to them, the patient may notify the healthcare provider of the adverse reaction. For instance, a message or prompt may be provided to the user requesting adverse reaction information. This information may then be sent to the healthcare provider in a secure message such as that described above.

In the example described above, the user initiated the compliance program for a medication or medical condition identified in the patient's electronic personal health record. Specifically, one or more of the compliance programs available to the healthcare provider may be configured such that they may be initiated by the user. In other words, the user may view and select one or more of the compliance programs for execution in association with the user. For instance, one or more of the compliance programs available to the healthcare provider may be marked (e.g., by the healthcare provider) to enable the user to self-enable the compliance program or, alternatively, prevent the user from self-enabling the compliance program. In the event that the user wishes to initiate such a compliance program, a notification may be transmitted to the healthcare provider informing the healthcare provider that the user has initiated the compliance program.

As described above, a compliance program may be initiated by the user or healthcare provider. Alternatively, execution of a compliance program may be automatically initiated when a particular event occurs. For instance, a particular compliance program may be automatically launched, or selected and initiated by the healthcare provider, when the healthcare provider generates or transmits a new message to the user, when an online consultation request is received, when an online consultation reply is generated or transmitted to the user, when a prescription renewal request is received, when an appointment request is received, when a prescription renewal reply is transmitted, when a general message is received from the user when a general message reply is transmitted to the user, when the user selects a particular medication or condition in his personal health record, or when a message is transmitted from a third party system such as a payor when a medication was not picked up or refilled after prescribed. In other words, the condition associated with one or more of the messages in a compliance program may be satisfied when information is received from a third party indicating that a prescription for the medication has not been filled or renewed as prescribed. The user may then be surveyed for the reason for non-compliance with respect to the non-fill or non-renewal action.

In addition to initiating execution of a particular compliance program, it may be desirable to disable (e.g., cancel) execution of a particular compliance program and/or in association with one or more users (even if already executing). This may be performed by the healthcare provider for a user or group of users, as well as all users. Similarly, the user may wish to disable execution of a particular compliance program that has been initiated for or by that user. This may be desirable, for example, if the user wishes to no longer receive the email notices that he or she has been receiving. When the user disables a particular compliance program, a notification may be transmitted to the healthcare provider informing the healthcare provider that the user has disabled the compliance program for the user. The healthcare provider may wish to reinitiate the compliance program, initiate a different compliance program, or contact the user in another more conventional manner. Moreover, it may be desirable to disable non-functioning compliance programs or those that are undergoing modifications (e.g., such as where new side-effects have been discovered in association with a particular medication).

In addition to the features described above with respect to compliance programs, the features available with respect to other online consultation messages are also available for use with compliance program messages. Thus, the compliance messages and electronic personal health record related messages may also be accessed in a secure manner by the user (and healthcare provider). In addition, the healthcare provider (e.g., physician) may assign permissions to other office staff to initiate or edit compliance programs as part of messaging permissions. In other words, one or more individuals associated with the healthcare provider (e.g., nurse, other physicians) may be given privileges such as read/write privileges. Moreover, the healthcare provider may store, view, and print messages from his or her in-box. Finally, for patients who are not online, there is the ability for a provider to generate and/or execute specific compliance programs that include a telephony-based component. In other words, a compliance program may include a telephony-based component and/or a component enabling secured messaging, e-mail or Internet communications. These programs and messages may be different from the web-based version of the programs. Alternatively, the messages may be the same or substantially equivalent to those provided in the web-based version of the programs. Patients will be able to receive compliance messages by phone (where the compliance messages are converted from text to voice), as well as communicate with the compliance program via phone. The telephony-based component may be automatically activated (or de-activated) by the provider for specific users and/or activated (or de-activated) by the user. Similarly, the "web-based" component may be automatically activated (or de-activated) by the provider for specific users and/or activated (or de-activated) by the user. In this manner, a compliance program may be set up to deliver messages via telephone (or other medium) to specific users (or all users). Patients will also be able to self-enroll or disenroll via phone, and providers will be able to enroll patients via the web.

Once the patient's health record is generated, the patient may choose to grant or (implicitly or explicitly) deny access to the patient's electronic personal health record or portion thereof to a particular healthcare provider or another individual. The access that is granted to a particular individual may be open-ended or may be temporary. For instance, the permission that is granted may be active until a particular date or for a particular number of times.

Figure 8:
FIG. 8 is an exemplary graphical user interface enabling a patient to grant access to the patient's electronic personal health record or portion thereof to an individual such as a healthcare provider.

FIG. 8 is an exemplary graphical user interface enabling a patient to grant access to the patient's electronic personal health record or portion thereof to an individual such as a healthcare provider. In this example, the patient (or caregiver) may grant or deny access by selecting a particular permission type for one or more individuals. In this example, each of the individuals is a healthcare provider (e.g., physician). For instance, the permission type may enable the individual to access the health record for an open-ended period of time, a single time, or until a specified date. Alternatively, the patient (or caregiver) may prevent the individual from accessing the patient's electronic personal health record by specifying that the individual has no access to view the patient's electronic personal health record by selecting the corresponding permission type.

For each individual who has been granted temporary access to the patient's health record, the patient (or caregiver) may generate a temporary ID and password, as shown. By using this temporary ID and password, the individual may access the patient's electronic personal health record for an unlimited length of time, until a particular date or for a particular number of times.

If the patient (or caregiver) wishes to limit the access that is granted (or denied) to a particular portion of the electronic personal health record, the patient (or caregiver) may identify those portions to which access has been granted (or denied). These portions may be designated via menu selections, pull-down menus, or other suitable mechanism.

In addition, the access that is granted (or denied) may be read, write, and/or forwarding access. Thus, depending upon the level of access, the grantee may be able to read the electronic personal health record (or portion(s) thereof) and may also be able to edit the electronic personal health record (or portion(s) thereof), as well as forward the electronic personal health record.

Figure 9:
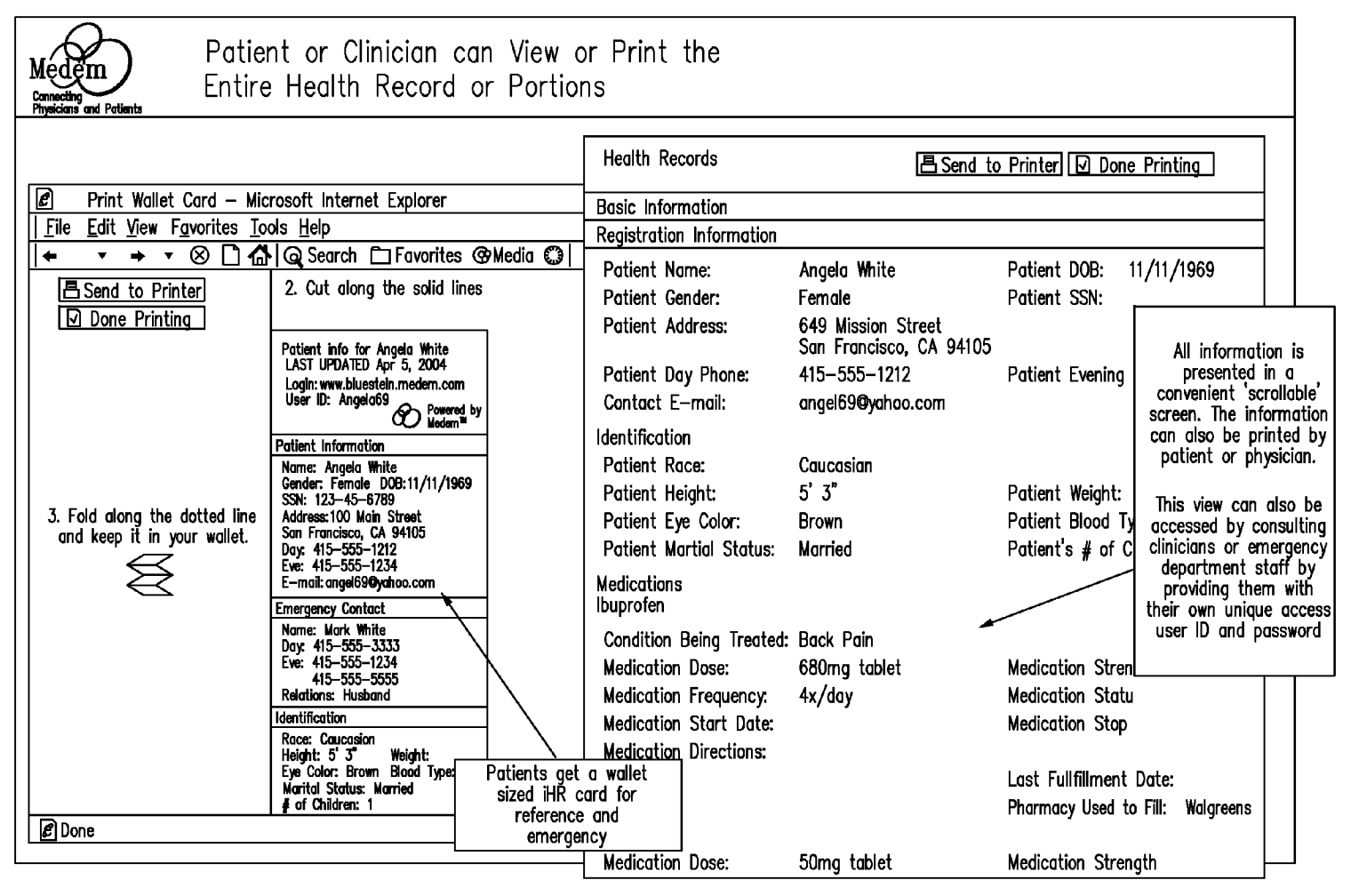

The patient (or caregiver) or other individual who has been granted access to the patient's electronic personal health record may access the patient's electronic personal health record by using his or her ID and password. FIG. 9 is an exemplary graphical user interface enabling a patient or other individual to view or print the patient's electronic personal health record or portion thereof. As shown, the information in the patient's electronic personal health record may be presented in a "scrollable" screen. The information presented may be printed by the patient (or caregiver) or healthcare provider. Moreover, a printable file or document may be generated from the electronic personal health record. In this manner, the patient may generate a printed electronic personal health record to provide to a healthcare provider (e.g., physician) of the patient. Moreover, the patient may also print a "wallet card," which contains information such as blood type, allergies, and emergency contact information for the patient, as well as any other information which the patient has selected to be contained in the wallet card.

Even when a healthcare provider has not been granted (or has been denied) access to a patient's electronic personal health record, the patient's electronic personal health record may still be accessed in an emergency situation. Specifically, the system may include an "override" capability in an emergency situation. For instance, the electronic personal health record may be accessed by consulting clinicians or emergency department staff by providing them with their own unique access user ID and password (e.g., which may be active for all electronic personal health records for all patients). Alternatively, the user ID and password may be provided by an emergency contact identified in the health record or "wallet card."

Once a patient's electronic personal health record has been accessed by a physician (or other individual), the physician may choose to print the health record or portion thereof. This may be desirable, for example, if the physician wants to print the information for the patient's physical file. In addition, the physician may wish to electronically prescribe a prescription or provide a prescription renewal based upon information in the health record.

Furthermore, the physician may also choose to generate a utilization report based upon information in patient health records. The utilization report may enable the physician to generate information pertaining to the patient health records to which he or she has access. For instance, the physicians may ascertain how many of their patients have an electronic personal health record, how many patients are taking a specific medication, or have a particular medical condition.

FIG. 10 is an exemplary printout representing an electronic personal health record registration form that may be used to replace the medical office clipboard. The patient or user may update the electronic personal health record, as well as print out the medical registration form and bring it to the provider's medical office for the scheduled appointment. In addition, if the electronic personal electronic personal health record system is integrated with the healthcare provider's electronic medical record system, an automatic or patient-initiated update of medical registration and/or other information associated with the patient may occur. In some embodiments, this information may automatically update the patient's electronic medical record maintained by the healthcare provider. In other embodiments, the healthcare provider may implicitly or explicitly accept or reject the information received from the patient's electronic personal health record before the information is stored in the patient's electronic medical record. In addition, a provider may print the medical registration information (e.g., if the provider has been granted access to the electronic personal health record).

Because the online medical registration process is built in to the electronic personal health record and will result in more complete information being available to the provider(s) at the time of care, and because this information represents administrative as well as clinical efficiency and efficacy for the provider, the provider may promote the electronic personal health record as the end of the medical clipboard. FIG. 11 is an exemplary graphic of the medical office promotion of the electronic personal health record representing no more clipboards to the patient.

Figure 12A:
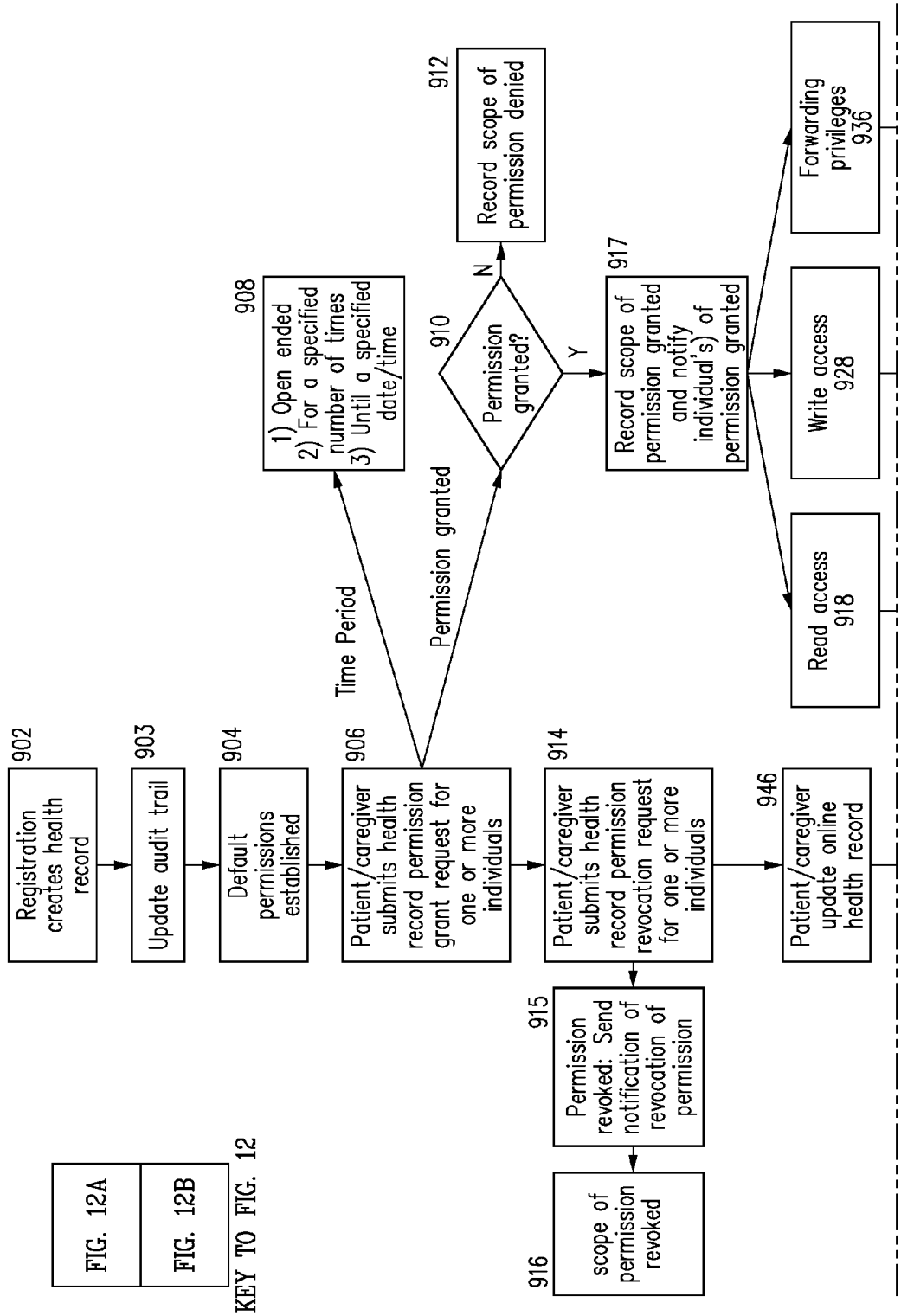
FIG. 12 is a process flow diagram illustrating a method of implementing an electronic personal health record system in accordance with one embodiment of the invention.
Figure 12B:
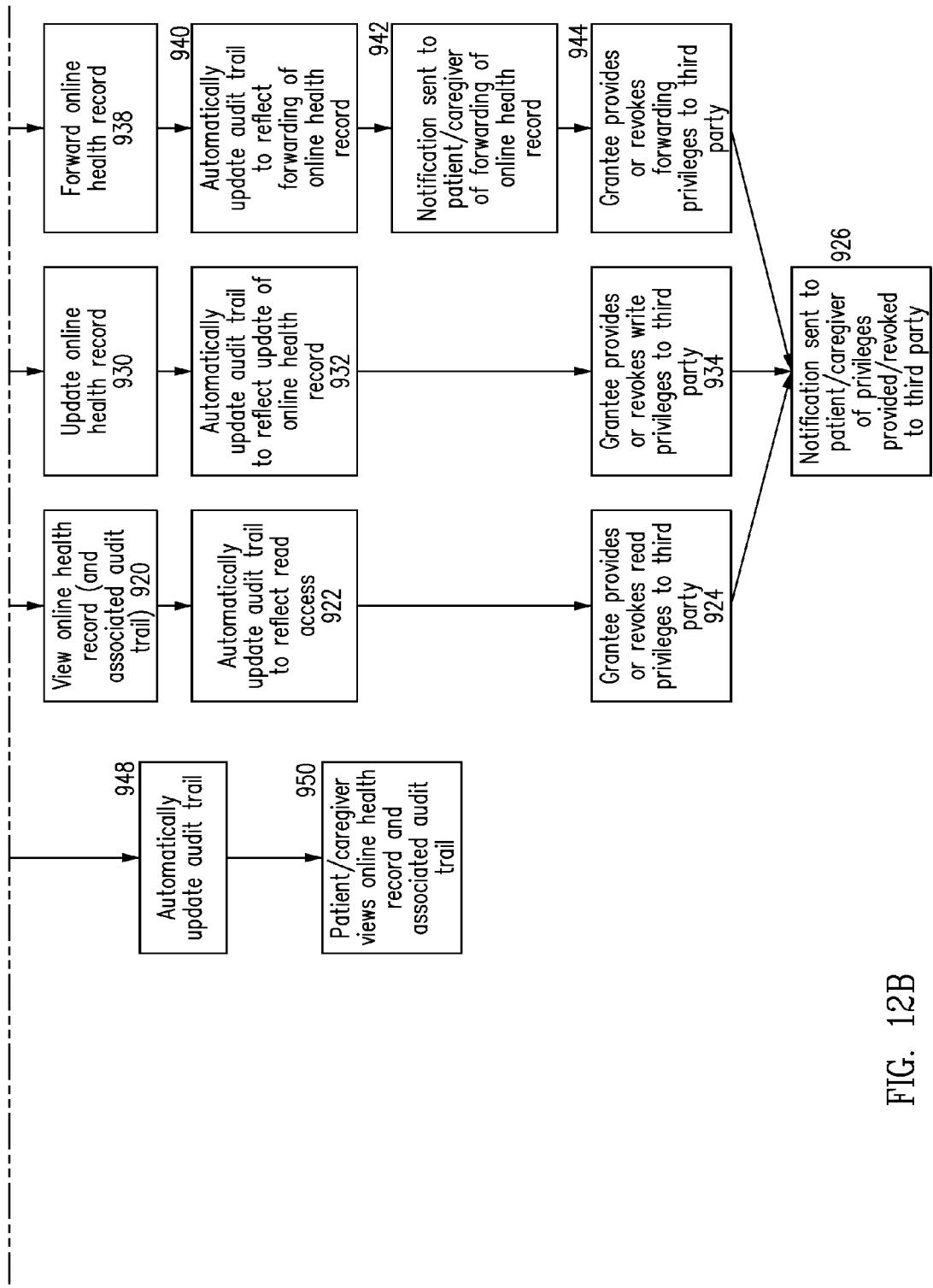

FIG. 12 is a process flow diagram illustrating a method of implementing an electronic personal health record system in accordance with one embodiment of the invention. As shown at block 902, the patient or caregiver may create the electronic personal health record via the physician's web site or central web site. For instance, the patient or caregiver may submit information from which the electronic personal health record may be generated. Alternatively, the electronic personal health record may be generated by a healthcare provider. For instance, the electronic personal health record may be generated, at least in part, from information obtained from the patient's paper file. As another example, the electronic personal health record may be populated from information obtained from a patient's initial registration with a physician's web site. Once generated, the electronic personal health record is available for access via the physician's web site (where applicable) and/or a central web site.

It may be desirable to request or require that the healthcare provider approve the electronic personal health record. Thus, the healthcare provider may be prompted to approve the electronic personal health record (e.g., the healthcare provider's notes or diagnoses). This prompting may be performed on a periodic (e.g., annual) basis. Moreover, the healthcare provider may establish the periodicity with which prompting is performed.

If the electronic personal health record is initially generated or populated by a healthcare provider, it may be desirable to obtain approval of the electronic personal health record from the patient or caregiver. This approval of the patient or caregiver may be obtained before the information is added to the electronic personal health record or before the information in the electronic personal health record is altered. Moreover, if they find any information in the electronic personal health record to be inaccurate or outdated, the patient or caregiver may modify the electronic personal health record. In addition, the patient may also delete their electronic personal health record at any time. In this manner, the patient may control access to their electronic personal health record. If the electronic personal health record has not been completed, a message may be sent to the patient or caregiver reminding them to complete or update the electronic personal health record. Moreover, it may be desirable to send a message to the healthcare provider indicating that the electronic personal health record is not completed, thereby enabling the healthcare provider to encourage the patient or caregiver to complete the electronic personal health record.

An audit trail may also be updated at block 903. The audit trail may, for example, denote a creation date and/or a creation time of the electronic personal health record. When the electronic personal health record is later accessed or altered, the audit trail may be updated. For instance, the audit trail may be subsequently updated to include a last edited date, a last edited time, an identifier of an individual who last edited the electronic personal health record, an identifier of each individual who viewed the electronic personal health record, a viewing date identifying a date that each individual viewed the electronic personal health record, an identifier of an individual associated with each portion of the electronic personal health record entered by the individual, an entered date indicating a date that the individual entered the portion of the electronic personal health record, and/or a source from which a portion of the electronic personal health record was transferred in association with the electronic personal health record such that the denoted information is visible to an individual accessing the electronic personal health record. Accordingly, the patient or caregiver (as well as other individuals) may be able to identify the time and originator of changes to the electronic personal health record, as well as identify individuals who have viewed the electronic personal health record.

Default permissions may be established automatically, or by the patient or caregiver, at block 904. For instance, the default may be to deny (or grant) access to all individuals. As another example, the default may be to deny access to all individuals other than the healthcare providers identified by the patient.

Default permissions may also be established when the patient (or caregiver) accesses the electronic personal health record via a web site of a particular physician. For instance, when the electronic personal health record is generated, updated or accessed via a physician's web site, the physician may be automatically granted permission to access the electronic personal health record. If the patient (or caregiver) chooses to change this default status, they can simply revoke the permission to access that was automatically granted to the physician.

The patient or caregiver (e.g., individual designated by the patient to manage the electronic personal health record of the patient) may choose to grant or deny permission to access the patient's electronic personal health record or portion thereof. This may be accomplished by designating a health record permission grant at block 906 for one or more individuals to establish the access privileges of the individuals. The health record permission grant may establish whether permission to access at least a portion of the electronic personal health record associated with the patient has been granted to one or more individuals. For instance, the permission to access that is granted (or denied) a particular individual may include read, write (e.g., including delete), and/or forwarding privileges. If the health record permissions deny access rights to a particular individual, permission to access the electronic personal health record (or portion thereof) is not granted to that individual.

As set forth above, the permission to access that is granted may be for only a portion of the electronic personal health record. This portion(s) may be identified by the patient or caregiver via a pull-down menu or other suitable mechanism.

In accordance with one embodiment, each physician with which the patient is registered (e.g., via the physician's web site) is identified, and the patient/caregiver is provided an option to grant permission to access the electronic personal health record to each physician with which the patient is registered. Once permission to access has been granted, the patient's electronic personal health record is available to the healthcare provider (e.g., via the practice view web site).

The time period 908 to which the health record permission grant pertains may be an unlimited (open-ended) period of time or a temporary period of time. For instance, the temporary period of time may correspond to a particular number of times (e.g., a single time) that the electronic personal health record may be accessed, or the time period may indicate that the grant is active until a specified date. In this matter, the grant may pertain to a limited period of time (or number of accesses). As set forth above, where access is granted for a limited period of time or number of accesses, a temporary ID and/or password may be generated (e.g., by the patient or caregiver) for access to the patient's electronic personal health record.

If the health record permission grant (e.g., submitted by the patient or caregiver) indicates that permission to access has not been granted at block 910, the scope of permission that has been denied is recorded at block 912. In other words, when the health record permission grant is made, an indication as to whether permission to access the electronic personal health record (or portion thereof) has been granted is recorded.

If the health record permission grant (e.g., submitted by the patient or caregiver) indicates that permission to access has been granted at block 910, the scope of the permission that has been granted to the individual(s) is recorded at block 917 and the individual(s) may be notified of the permission to access that has been granted. For instance, the individual(s) may be reminded to access the electronic personal health record.

As shown at block 918, if an individual has been granted read access, the individual may view the electronic personal health record (or portion thereof) as well as the associated audit trail at block 920. The individual may also choose to export data from the electronic personal health record. For instance, this data may be used to populate another record such as an online consultation record. The audit trail may be automatically updated at block 922 to reflect the read access, as set forth above with respect to block 903.

When the individual who has been granted read access is a healthcare provider, the healthcare provider may choose to filter electronic personal health records (or patients) according to information in the electronic personal health records, such as the medical conditions and/or medications listed in the electronic personal health records. The healthcare provider may then choose to initiate a compliance program for these patients in accordance with these selected conditions and/or medications, age ranges and/or sex. As set forth above, a compliance program includes one or more messages to be transmitted to the patient or caregiver when a condition (e.g., time period) associated with the corresponding message is satisfied, where each of the messages includes medical advice or medical information corresponding to a medication and/or medical condition.

In accordance with one embodiment, when permission to access at least a portion of the electronic personal health record has been granted to an individual by the patient or the patient's caregiver, that individual may choose to grant access to another third-party. For instance, a healthcare provider or other "grantee" to whom the patient has previously provided permission to access the electronic personal health record (or portion thereof) may invoke a health record permission grant. Of course, the grantee will preferably only be able to grant a level of access that is less than or equal to the privileges that have previously been provided to the grantee. This additional grant permission may be provided as an option to the patient or caregiver, thereby enabling the patient or caregiver to select those individuals who have this additional "grant" privilege. Moreover, this additional grant permission may only be available for healthcare providers to whom access privileges have been granted. Once this additional grant has been made, a notification may be sent to the patient and/or caregiver indicating that the health record permission was submitted by the grantee (e.g., healthcare provider). In addition, the patient or caregiver may choose to override this "grant" by the "grantee."

Once a grant has been received from a grantee, the grantee may later choose to revoke this permission that has been granted to another third-party. Specifically, a health record permission revocation may be made by a grantee (e.g., healthcare provider) to whom the patient (or caregiver) has previously granted access to the electronic personal health record (or portion thereof), as well as the patient. Once this revocation has been made, a notification may be sent to the patient and/or caregiver indicating that the health record permission revocation has been made by the grantee (e.g., healthcare provider).

As shown at block 924, a grantee may choose to grant (or revoke) read access privileges to another third-party. A notification may then be sent to the patient and/or caregiver at block 926 of the read privileges that have been granted to the third-party by the grantee (e.g., healthcare provider) or revoked by the grantee.

As shown at block 928, if an individual has been granted write access, the individual may edit and/or delete portions of the electronic personal health record (or portion thereof). When the individual is a healthcare provider, the healthcare provider may choose to associate or "attach" a particular document with the electronic personal health record, as well as import data from another data source (e.g., electronic medical record, e-prescribing system, or lab or x-ray results). Moreover, the healthcare provider may wish to add notes or other information to the electronic personal health record. It may also be desirable to prompt the healthcare provider to update the electronic personal health record on a periodic basis (e.g., annual basis). The healthcare provider may establish the periodicity with which the prompting is performed, or if the provider has an electronic medical record system that interfaces with the electronic personal health record system, the system may automatically conduct updates between the electronic personal health record and electronic medical record. These updates that are received may be automatically incorporated or incorporated upon acceptance by the patient (or caretaker) or healthcare provider, respectively. The electronic personal health record is then updated at block 930 to reflect the editing that has occurred. In accordance with one embodiment, the patient or caregiver must accept changes made to the health record before the health record is updated. Thus, the electronic personal health record is updated with information that has been received from the individual (e.g., healthcare provider). In addition, the audit trail may be automatically updated at block 932 to reflect the write access, as set forth above with respect to block 903.

As shown at block 934, a grantee may choose to grant (or revoke) write access privileges to another third-party. A notification may then be sent to the patient and/or caregiver at block 926 of the write privileges that have been granted to the third-party by the grantee (e.g., healthcare provider) or revoked by the grantee.

As shown at block 936, if an individual has been granted forwarding privileges, the individual may forward the electronic personal health record (or portion thereof) at block 938, or otherwise submit a request that it be forwarded to a particular third-party (e.g., another healthcare provider). The audit trail may be automatically updated at block 940 to indicate that the electronic personal health record (or portion thereof) has been forwarded (e.g., to a particular individual), as set forth above with respect to block 903. A notification may then be sent to the patient and/or caregiver indicating that the electronic personal health record (or portion thereof) was forwarded to the third-party at block 942.

As shown at block 944, a grantee may choose to grant (or revoke) forwarding privileges to another third-party. A notification may then be sent to the patient and/or caregiver at block 926 of the forwarding privileges that have been granted to the third-party by the grantee (e.g., healthcare provider) or revoked by the grantee.

If the patient or caregiver later chooses to revoke access privileges that have previously been granted to an individual, the patient or caregiver may make a health record permission revocation at block 914 that revokes the permission that was previously granted to the individual, either by the patient or another "grantee." At that time, it may be desirable to notify that individual that the permission to access the patient's electronic personal health record that was previously granted has been revoked at block 915. The scope of the permission that has been revoked is recorded at block 916.

At any time, the patient (or caregiver) may choose to update the patient's electronic personal health record at block 946. For instance, the patient (or caregiver) may choose to associate or "attach" a document or photograph to the online personal health record. Moreover, the patient (or caregiver) may submit information, such as a message to a healthcare provider, or a comment associated with data in the electronic personal health record. It may be desirable to prompt the patient and/or caregiver to update the electronic personal health record on a periodic basis. For instance, a message may be sent to the patient or caregiver reminding them to complete (or update) the electronic personal health record. A healthcare provider may then approve the information received from the patient/caregiver. The audit trail may then be automatically updated accordingly at block 948, as set forth above with reference to block 903. The patient/caregiver may view the electronic personal health record and associated audit trail at any time, as shown at block 950.

In accordance with the above-described embodiments, it is assumed that electronic mail is an insecure medium and may be easily intercepted. Communication is therefore implemented in a two-tier communication process via e-mail notification and a secure, authenticated environment on the physician web site (or central web site) (e.g., secure messaging system). However, it is important to note that physician-patient communications may also be transmitted via e-mail, such as using an encrypted e-mail system, or other secure communication system. In this manner, the present invention enables online physician-patient communications to comply with federally mandated privacy requirements such as HIPAA.

As described above, the patient's electronic personal health record may be updated with information received from a variety of third-party sources, including, but not limited to, payors and healthcare providers. This information may be automatically sent, or may be transmitted upon initiation by a user (e.g., patient, healthcare provider, payor, etc.).

Figure 13:
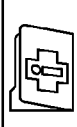
FIG. 13 is an exemplary graphical user interface of the patients' view of third party data that has been sent to update the electronic personal health record.

FIG. 13 is an exemplary graphical user interface of the patients' view of third party data that has been sent to update the electronic personal health record. In this example, clinical information is automatically transferred from the provider's electronic medical record for incorporation into the electronic personal health record. Since the content of the electronic personal health record is controlled by the patient (or caregiver), the patient is given the opportunity to review this information and decide whether or not they want to update their electronic personal health record with this information. The information may be implicitly or explicitly accepted or rejected by the patient, in whole or in part, thereby enabling the patient to indicate which information, if any, can be added to their electronic personal health record. In this example, the patient has chosen to update his electronic personal health record with conditions and medications from the provider's electronic medical record. However, the patient has implicitly rejected the information associated with the allergies, immunizations, and surgeries/procedures by not checking the associated boxes, as shown. Once the patient accepts all of the information, indicates which information they will accept, or declines the information, the electronic personal health record is updated (or not) accordingly. Third party data from an electronic medical record may be provided from a variety of providers in the healthcare system, including physicians, hospitals, medical centers, etc. Similarly, information stored in the electronic personal health record may be sent for incorporation into the provider-maintained electronic medical record from time to time. The healthcare provider (e.g., physician or designated reviewer such as a practice administrator or nurse practitioner) may review the information and decide whether the information, in whole or in part, will be accepted for population into the patient's electronic medical record. In this way, the patient maintains complete control of their electronic personal health record, and the provider maintains complete control of the electronic medical record.

Information that is retrieved or transmitted from a third party system may be obtained via a variety of mechanisms, such as a user selection, link or other graphical user interface. As will be described in further detail below with reference to FIG. 14, information may be shared between a patient-controlled electronic personal health record and a healthcare provider-controlled electronic medical record. It is important to note that this example is merely illustrative, and therefore information may be shared among a variety of electronic systems, including, but not limited to, a patient-controlled electronic personal health record system, healthcare provider-controlled electronic medical record system, and other third party systems such as payors (e.g., insurers, Medicare, etc.).

FIG. 14 is an exemplary graphic of an electronic personal health record containing links to third party provider systems, which may contain more detailed clinical information on the patient. For instance, in this example, links to the patient's medical record maintained by St. Joseph Hospital, San Michael Hospital, Paragon Labs, and Emmitt Cardiology are provided. As shown in this example, the patient-centric electronic personal health record may serve as a patient-specific and clinically relevant front end to data sharing and patient information access, and may serve as a platform for the exchange of patient information between any/all approved healthcare providers, as well as other third parties, such as payors. This embodiment serves to resolve the more complicated large clinical repository of patient information established in the past, by enabling integration and information sharing among an online, patient-centric electronic personal health record and third party data repositories such as payor or healthcare provider repositories. In addition, patient authorization of access to information contained within the electronic personal health record solves HIPAA patient consent issues associated with the clinical data sharing.

Figure 15:
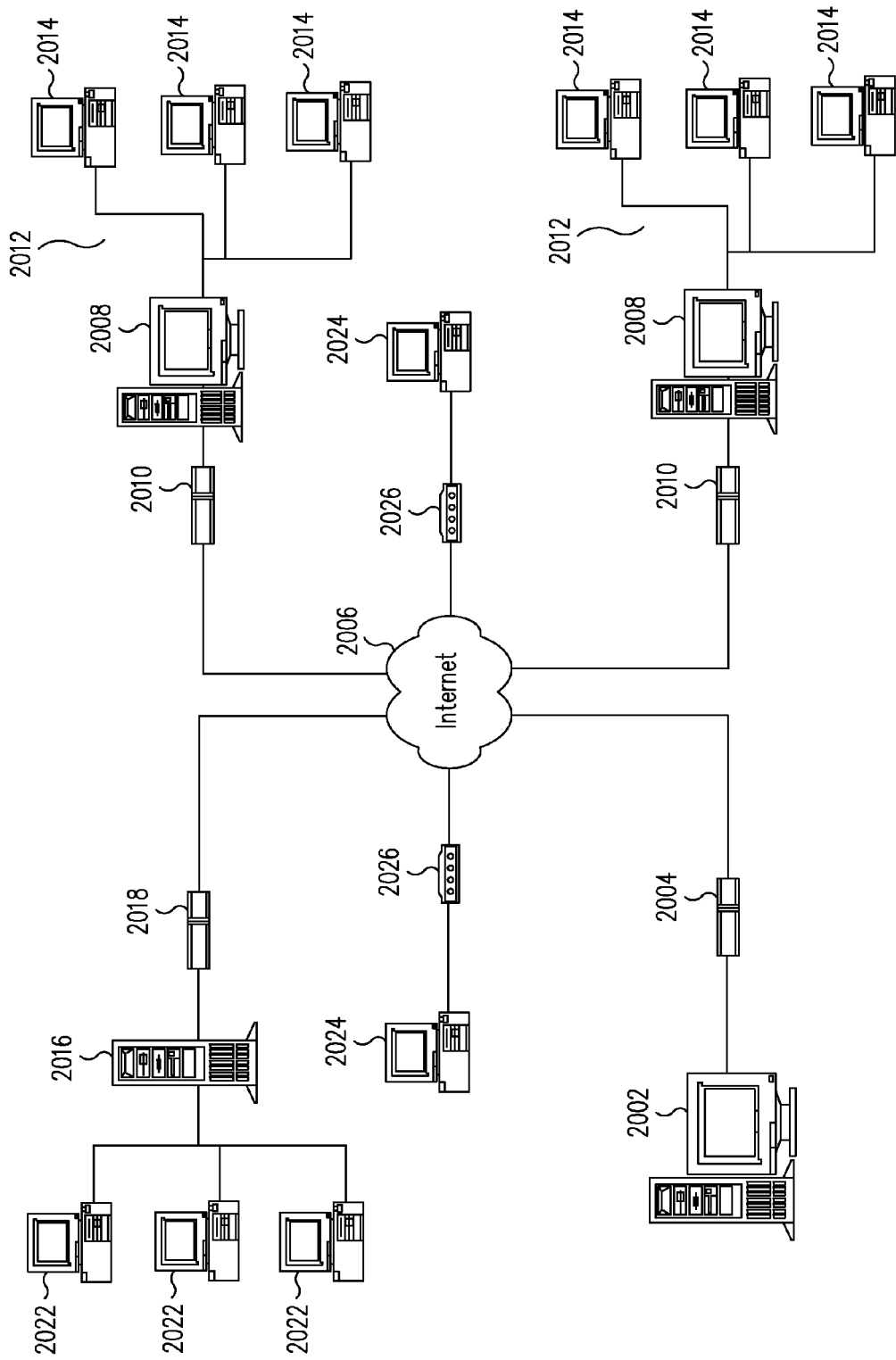
FIG. 15 is a diagram illustrating an exemplary system in which the present invention may be implemented.

FIG. 15 is a block diagram of a hardware environment in which the various embodiments of the present invention may be implemented. The web site at which communications between users and one or more providers (e.g. physicians) are facilitated according to the invention is located on a server 2002, which is connected by a router 2004 to the Internet 2006. Each individual physician's web site is hosted by the server 2002. In addition, physician office servers 2008 may also be connected to the Internet via routers 2010 in order to receive the transmission of e-mails, online consultation messages, compliance messages, and messages among physicians and patients related to electronic personal health records from the server 2002. The physician office servers 2008 may run software as well as store secure messages such as online consultation request and/or reply messages. For instance, it may be desirable to download online consultation request and/or partially completed reply messages, prepare online consultation reply messages, and upload those online consultation reply messages upon completion, as well as view or upload an electronic personal health record, import data into the electronic personal health record, and export data from the electronic personal health record. Physician office servers 2008 may have networks 2012 associated therewith interconnecting a plurality of personal computers or work stations 2014. In this manner, an office network may access the server 2002. User-patients (represented by computers 2022 and 2024) may be connected to the Internet in a variety of ways. For example, a patient may be connected from his home via a modem 2026, or from his workplace via a network 2020, a file server 2016, and a router 2018. It will be understood that, according to various embodiments of the invention, patients may gain access to the web site on server 2002 via a variety of hardware configurations. Similarly, businesses may be coupled to the web site on server 2002 in order to receive the transmission of communications such as e-mails from the web site. For example, a business may consist of an individual on his home computer 2024 or other device, such as a pager, phone or other hand-held device. Similarly, a consumer may be an employee who accesses the web site from his computer 2014 at his place of employment which is a business. It will also be understood that the hardware environment of FIG. 31 is shown for illustrative purposes and that a wide variety of hardware environments may be employed to implement the various embodiments of the present invention. It should also be understood that specific embodiments of the methods and processes described herein are implemented as computer program instructions, i.e., software, in the memory of server 2002.

Various embodiments of the invention can also be embodied as computer readable code on a computer readable medium. The computer readable medium is any data storage device that can store data, which can thereafter be read by a computer system. Examples of the computer readable medium include read-only memory, random-access memory, CD-ROMs, magnetic tape, and optical data storage devices.

Although illustrative embodiments and applications of this invention are shown and described herein, many variations and modifications are possible which remain within the concept, scope, and spirit of the invention, and these variations would become clear to those of ordinary skill in the art after perusal of this application. For instance, the present invention is based upon the generation and transmission of online consultation messages, compliance messages, and electronic personal health record communications using a two-tier system, preferably in the form of electronic mail and via a physician's web site. However, it should be understood that the present invention is not limited to this arrangement, but instead would equally apply regardless of the mode of transmission or system configuration. Moreover, it should be understood that "messages" such as electronic personal health record permission grant and revocation requests may be implemented in a variety of ways including, but not limited to, menu selections and other graphical user interfaces. In addition, the above-described embodiments may be implemented in a variety of languages. Accordingly, the present embodiments are to be considered as illustrative and not restrictive, and the invention is not to be limited to the details given herein, but may be modified within the scope and equivalents of the appended claims.

What is claimed is:

1. A system for managing an electronic healthcare record comprising:
   a healthcare computing system having healthcare information about a patient stored therein, access to the healthcare information being under the control of the patient, the healthcare computing system being configured to execute a process for controlling access to the healthcare information, the process for controlling access to the healthcare information comprising:
   receiving first information from the patient granting a first healthcare provider access to at least a portion of the healthcare record, thereby creating a first healthcare provider portion;
   receiving second information from the first healthcare provider granting a second healthcare provider access to at least a portion of the first healthcare provider portion;
   wherein the healthcare computing system is configured to only allow the second healthcare provider access to the at least a portion of the first healthcare provider portion once the second information is received;
   wherein the access grant associated with the first healthcare provider is one of read access, write access, and forwarding access, and
   the access grant provided by the first healthcare provider and associated with the second healthcare provider does not exceed the rights granted to the first healthcare provider.

2. The system for managing an electronic healthcare record of claim 1 wherein
   access to the second healthcare provider is granted only for a temporary period of time including the period beginning when access is granted and ending at a specified date.

3. The system for managing an electronic healthcare record of claim 1 wherein
   access to the second healthcare provider is granted only for a limited number of accesses.

4. The system for managing an electronic healthcare record of claim 1 wherein
   receiving, by the patient, indication regarding the second healthcare being granted access; and
   receiving, at the healthcare computing system an indication from the patient to override the access granted to the second healthcare provider by the first healthcare provider.

5. A computer program product for managing an electronic healthcare record comprising:
   a nontransitory computer readable medium;
   and computer program code, encoded on the computer readable medium, comprising computer readable instructions for:

a healthcare computing system having healthcare information about a patient stored therein, access to the healthcare information being under the control of the patient, the healthcare computing system being configured to execute a process for controlling access to the healthcare information, the process for controlling access to the healthcare information comprising:

receiving first information from the patient granting a first healthcare provider access to at least a portion of the healthcare record, thereby creating a first healthcare provider portion;

receiving second information from the first healthcare provider granting a second healthcare provider access to at least a portion of the first healthcare provider portion;

wherein the healthcare computing system is configured to only allow the second healthcare provider access to the at least a portion of the first healthcare provider portion once the second information is received;

wherein the access grant associated with the first healthcare provider is one of read access, write access, and forwarding access, and the access grant provided by the first healthcare provider and associated with the second healthcare provider does not exceed the rights granted to the first healthcare provider.

6. The computer program product for managing an electronic healthcare record of claim 5 wherein access to the second healthcare provider is granted only for a temporary period of time including the period beginning when access is granted and ending at a specified date.

7. The computer program product for managing an electronic healthcare record of claim 5 wherein access to the second healthcare provider is granted only for a limited number of accesses.

8. The computer program product for managing an electronic healthcare record of claim 5 wherein receiving, by the patient, indication regarding the second healthcare being granted access; and receiving, at the healthcare computing system an indication from the patient to override the access granted to the second healthcare provider by the first healthcare provider.

* * * * *